(12) United States Patent
Kakehata et al.

(10) Patent No.: US 10,774,003 B2
(45) Date of Patent: Sep. 15, 2020

(54) SURFACE STRUCTURE FORMING METHOD FOR ZIRCONIA-BASED CERAMICS, AND ZIRCONIA-BASED CERAMICS

(71) Applicant: National Institute of Advanced Industrial Science and Technology, Tokyo (JP)

(72) Inventors: Masayuki Kakehata, Tsukuba (JP); Hidehiko Yashiro, Tsukuba (JP); Isao Matsushima, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 323 days.

(21) Appl. No.: 15/510,198

(22) PCT Filed: Sep. 10, 2015

(86) PCT No.: PCT/JP2015/075732
§ 371 (c)(1),
(2) Date: Mar. 9, 2017

(87) PCT Pub. No.: WO2016/039419
PCT Pub. Date: Mar. 17, 2016

(65) Prior Publication Data
US 2017/0260100 A1    Sep. 14, 2017

(30) Foreign Application Priority Data
Sep. 11, 2014   (JP) .................................. 2014-185472

(51) Int. Cl.
*C04B 35/48* (2006.01)
*C04B 41/91* (2006.01)
(Continued)

(52) U.S. Cl.
CPC ................ *C04B 35/48* (2013.01); *A61C 8/00* (2013.01); *A61C 8/0012* (2013.01);
(Continued)

(58) Field of Classification Search
None
See application file for complete search history.

(56) References Cited

U.S. PATENT DOCUMENTS 6,057,525 A * 5/2000 Chang .................. B23K 26/032
219/121.73
7,875,414 B2   1/2011 Sawada et al.
(Continued)

FOREIGN PATENT DOCUMENTS

CN    101264550 A    9/2008
JP    H8-45114 A     2/1996
(Continued)

OTHER PUBLICATIONS

Fumiya Watanabe, et al.: Ablation of crystalline oxides by infrared femtodecond laser pulses: Journal of Applied Physics, 100, 083519 (Year 2006).*
(Continued)

*Primary Examiner* — Matthew J Daniels
*Assistant Examiner* — Mohammad M Ameen
(74) *Attorney, Agent, or Firm* — Studebaker & Brackett PC

(57) ABSTRACT

Provided herein is a method for forming a periodic microstructure on a surface of zirconia-based ceramics, which are not easily mechanically workable, without causing thermal adverse effects. A zirconia-based ceramic having a surface periodic microstructure is also provided. A linearly or circularly polarized laser beam is irradiated to a zirconia-based ceramic surface, and periodic irregularities are formed in a spot of the laser beam. Stripe-pattern irregularities parallel to
(Continued)

the direction of polarization can be formed in a spot of a laser beam by irradiating a linearly polarized ultrashort pulsed-laser beam to a zirconia-based ceramic surface. A mesh-like raised region and a dot-like recessed region can be periodically formed by irradiating a circularly polarized ultrashort pulsed-laser beam to a ceramic surface.

20 Claims, 11 Drawing Sheets

(51) Int. Cl.
  *B23K 26/352* (2014.01)
  *A61F 2/30* (2006.01)
  *A61C 8/00* (2006.01)
  *A61C 13/00* (2006.01)
  *C04B 41/00* (2006.01)

(52) U.S. Cl.
  CPC ............ *A61C 13/0018* (2013.01); *A61F 2/30* (2013.01); *B23K 26/352* (2015.10); *C04B 41/009* (2013.01); *C04B 41/0036* (2013.01); *C04B 41/91* (2013.01); *A61C 2008/0046* (2013.01); *C04B 2235/3244* (2013.01); *C04B 2235/963* (2013.01)

(56) References Cited

U.S. PATENT DOCUMENTS

| | | | |
|---|---|---|---|
| 8,728,585 B2 | 5/2014 | Sawada et al. | |
| 2006/0138102 A1* | 6/2006 | Sawada | B23K 26/0643 219/121.69 |
| 2008/0124486 A1 | 5/2008 | Sawada et al. | |
| 2008/0218829 A1 | 9/2008 | Nakamura | |
| 2009/0035723 A1* | 2/2009 | Daniel | A61L 27/50 433/215 |
| 2012/0018993 A1* | 1/2012 | Boegli | B23K 26/0624 283/74 |
| 2014/0063609 A1* | 3/2014 | Iwata | G02B 1/118 359/601 |

FOREIGN PATENT DOCUMENTS

| | | | |
|---|---|---|---|
| JP | 09-048684 | * | 2/1997 |
| JP | H09-048684 A | | 2/1997 |
| JP | 2003-057422 A | | 2/2003 |
| JP | 2003-211400 A | | 7/2003 |
| JP | 4054330 B2 | | 2/2008 |
| JP | 2008-170679 A | | 7/2008 |
| JP | 2008-216911 A | | 9/2008 |
| JP | 4440270 B2 | | 3/2010 |

OTHER PUBLICATIONS

An Office Action mailed by the Japanese Patent Office dated Apr. 3, 2019, which corresponds to Japanese Patent Application No. 2016-547502 and is related to U.S. Appl. No. 15/510,198; with English translation.

International Search Report issued in PCT/JP2015/075732; dated Nov. 2, 2015.

Writtteon Opinion issued in PCT/JP2015/075732; dated Nov. 2, 2015.

Delgado-Ruíz et al.; Femtosecond laser microstructuring of zirconia dental implants; Journal of Biomedical Materials Research B; Applied Biomaterials; Jan. 2011; pp. 91-100; vol. 96B; Issue 1.

Höhm et al.; Femtosecond laser-induced periodic surface structures on silica; Journal of Applied Physics 112; 2012; pp. 014901-1 to 014901-9.

Watanabe et al; Ablation of crystalline oxides by infrared femtosecond laser pulses; Journal of Applied Physics 100; 2006; pp. 083519-1 to 083519-6.

Kawamura et al.; Fabrication of surface relief gratings on transparent dielectric materials by two-beam holographic method using infrared femtosecond laser pulses; Applied Physics B lasers and Optics; Jul. 2000; pp. 119-121.

Heiroth et al.; Laser ablation characteristics of yttria-doped zirconia in the nanosecond and femtosecond regimes; Journal of Applied Physics 107; 2010; pp. 014908-1 to 014908-10.

Ihlemann et al.; Nanosecond and femtosecond excimer-laser ablation of oxide ceramics; Applied Physics A; 1995; pp. 411-417; vol. 60.

Kawahara et al.; Sub-micrometer surface dot structure formation by femtosecond laser irradiation; Canon Machinery Inc., research and development center; Sep. 4, 2006; pp. 881-882.

The extended European search report issued by the European Patent Office dated May 15, 2018, which corresponds to European Patent Application No. 15839233.2-1126 and is related to U.S. Appl. No. 15/510,198.

An Office Action; "Notification of Reasons for Refusal," issued by the Japanese Patent Office dated May 9, 2018, which corresponds to Japanese Patent Application No. 2016-547502 and is related to U.S. Appl. No. 15/510,198; with English translation.

Office Action issued by the Japanese Patent Office dated Jul. 6, 2020, which corresponds to Japanese Patent Application No. 2019-118665 and is related to U.S. Appl. No. 15/510,198; with English translation.

* cited by examiner

[FIG. 1]
(a)
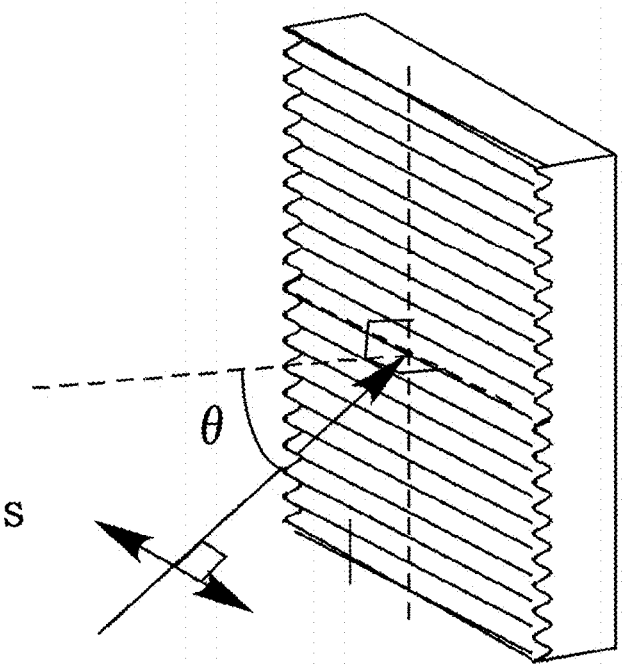
(b)
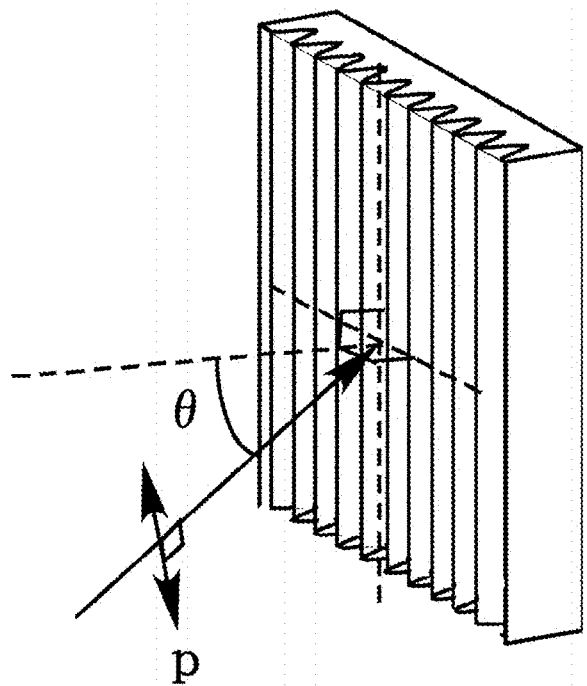

[FIG. 2]
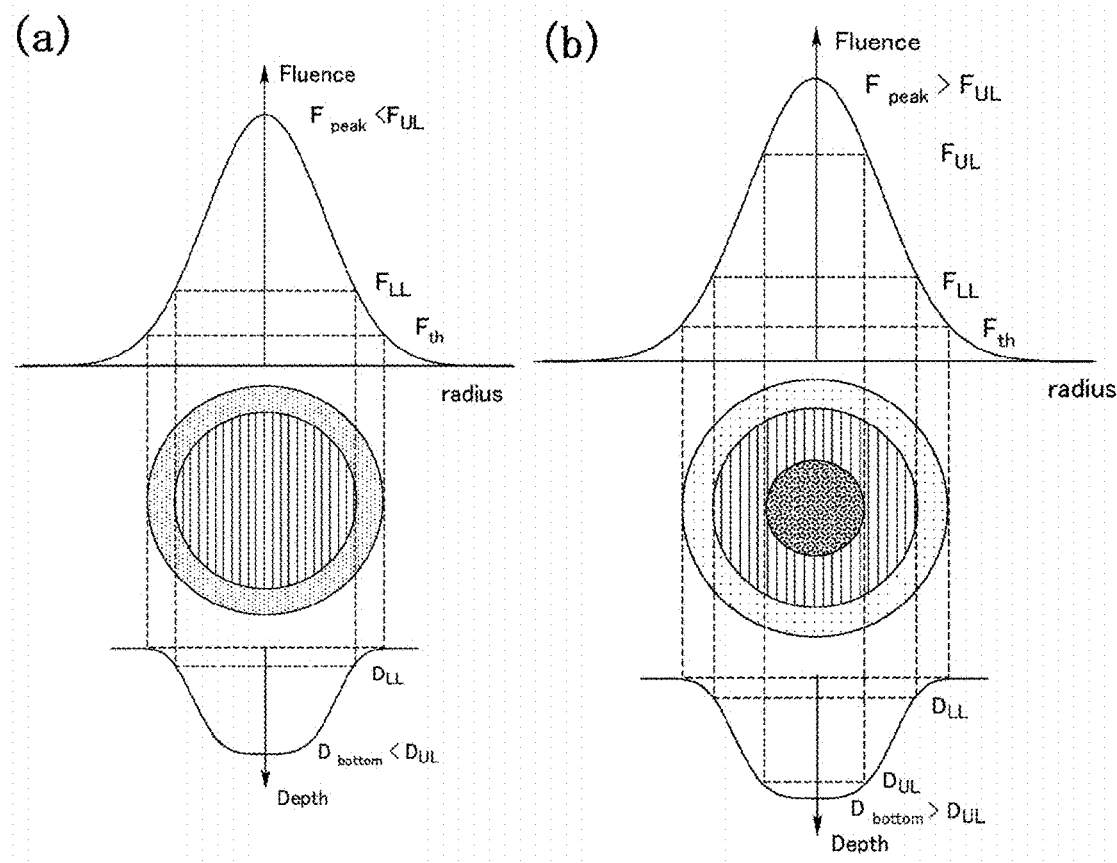
[FIG. 3]
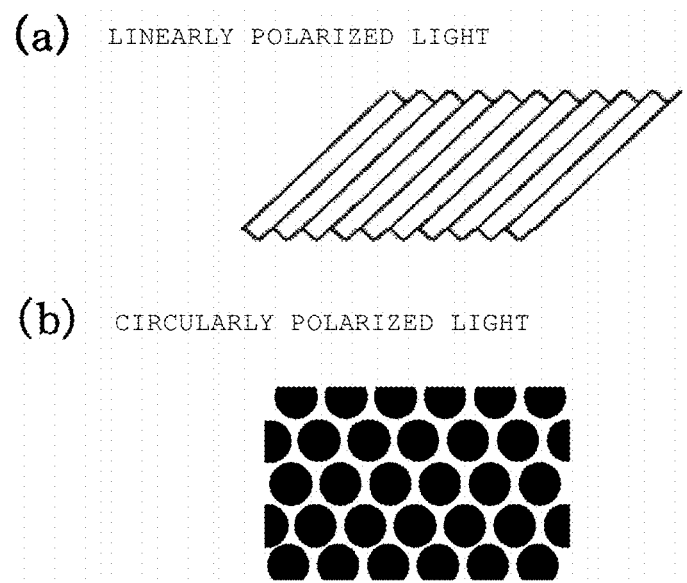

[FIG. 4]
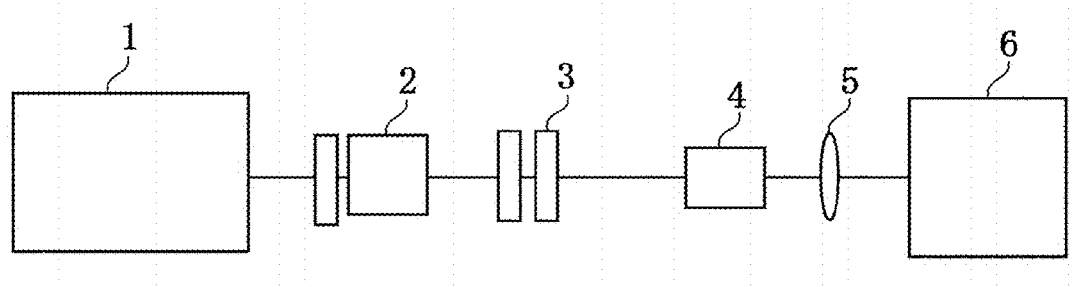
[FIG. 5]

[FIG. 6]
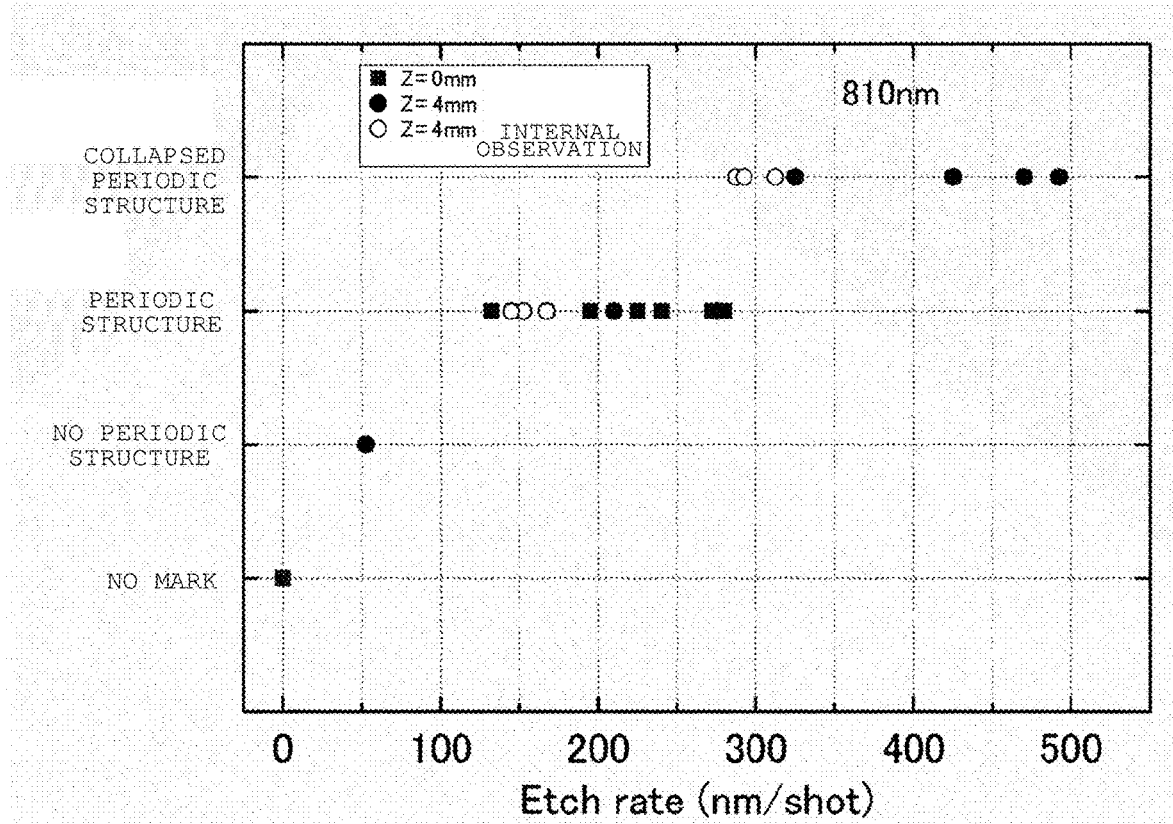
[FIG. 7]
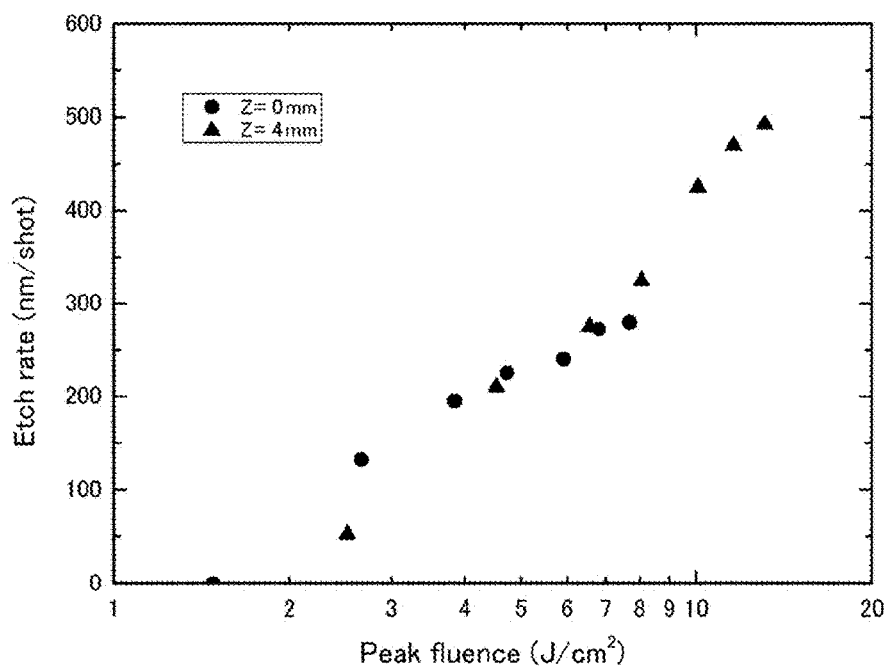

[FIG. 8]
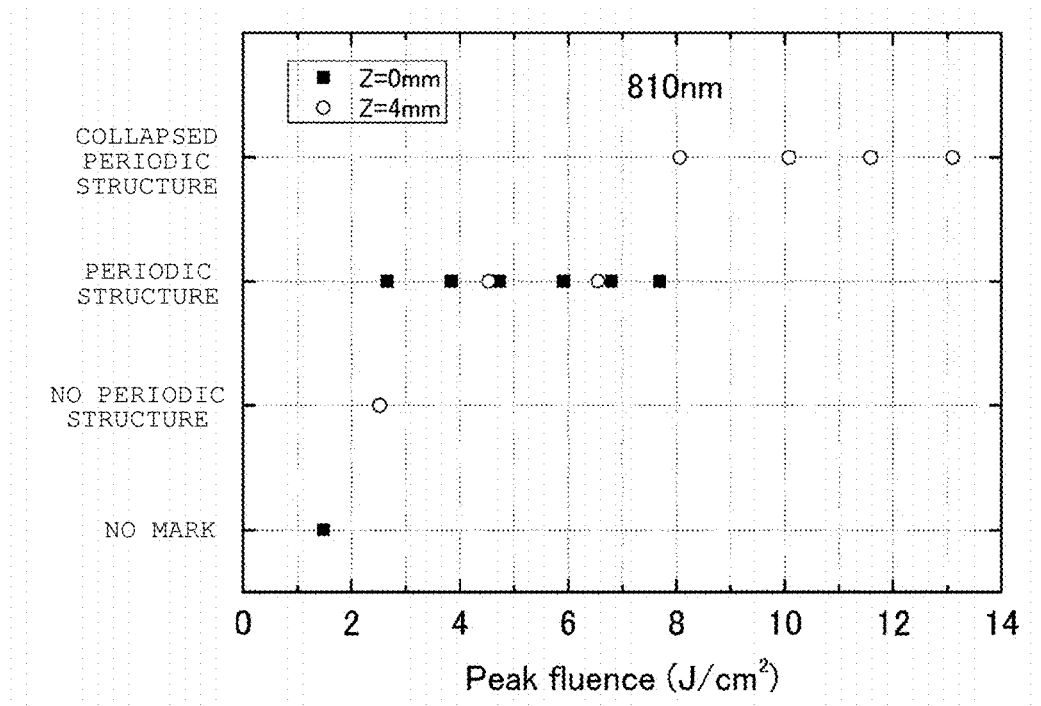
[FIG. 9]
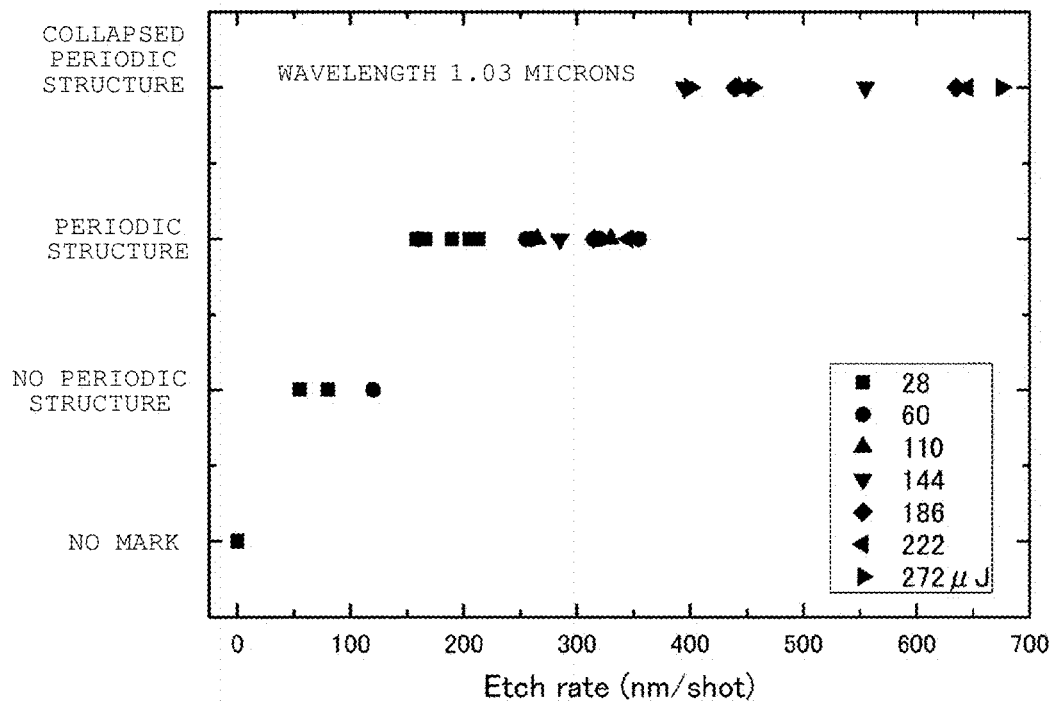

[FIG. 10]
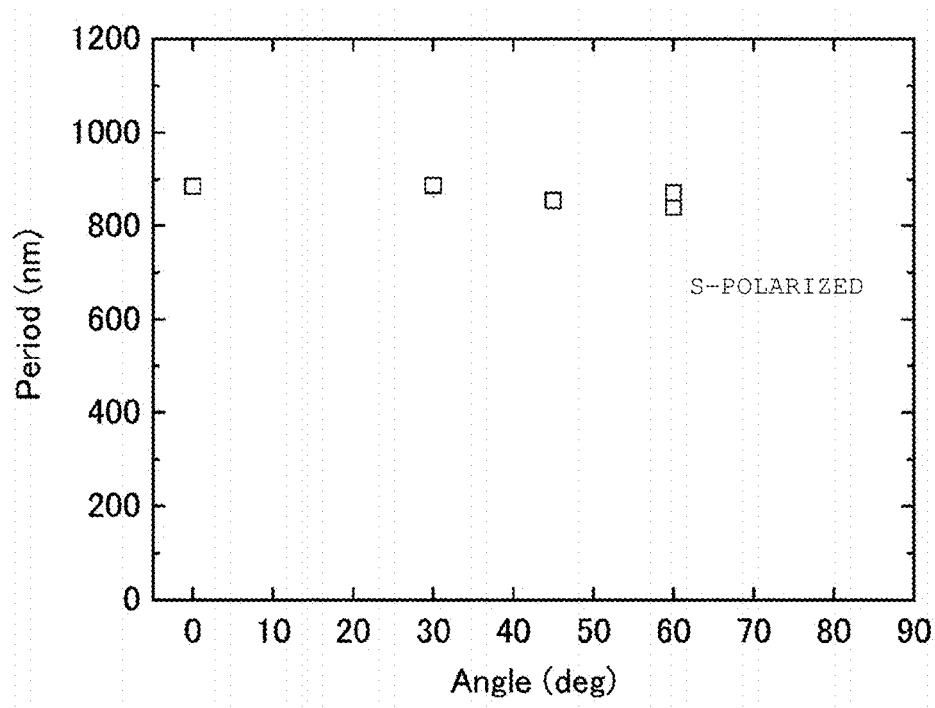
[FIG. 11]
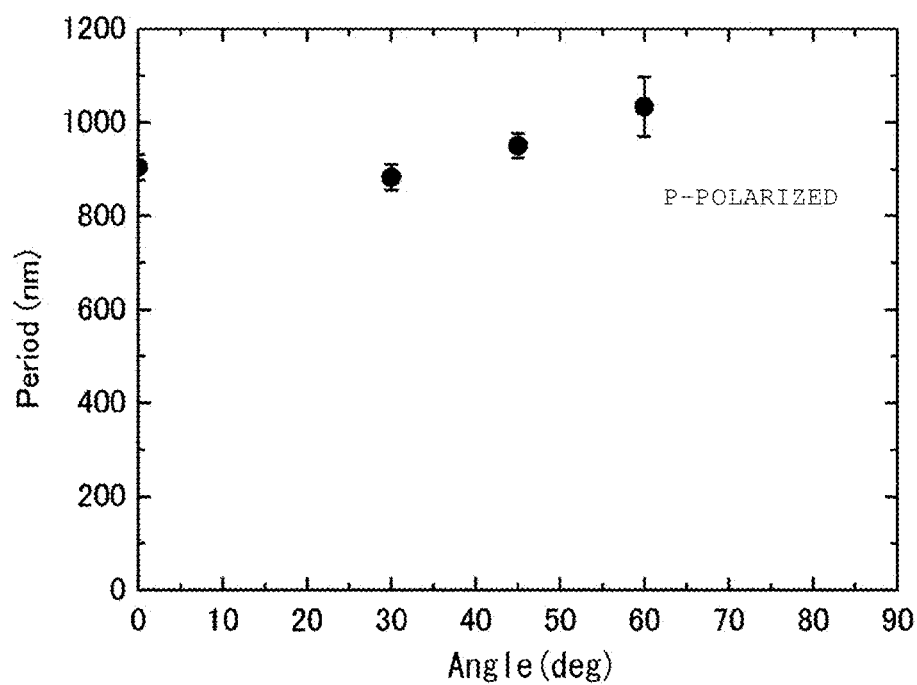

[FIG. 12]
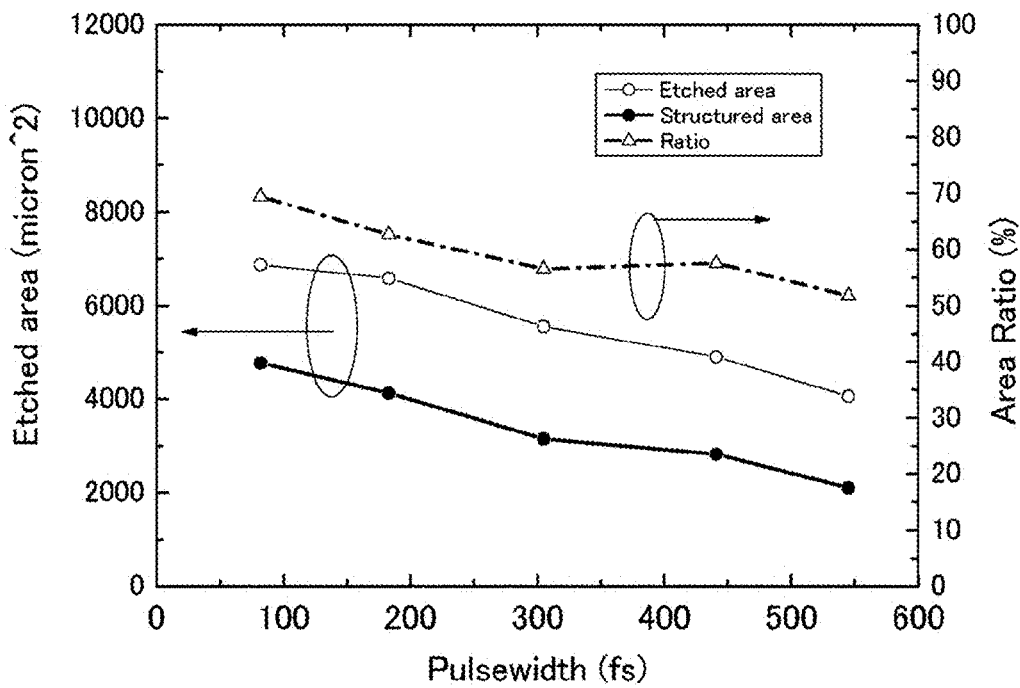
[FIG. 13]
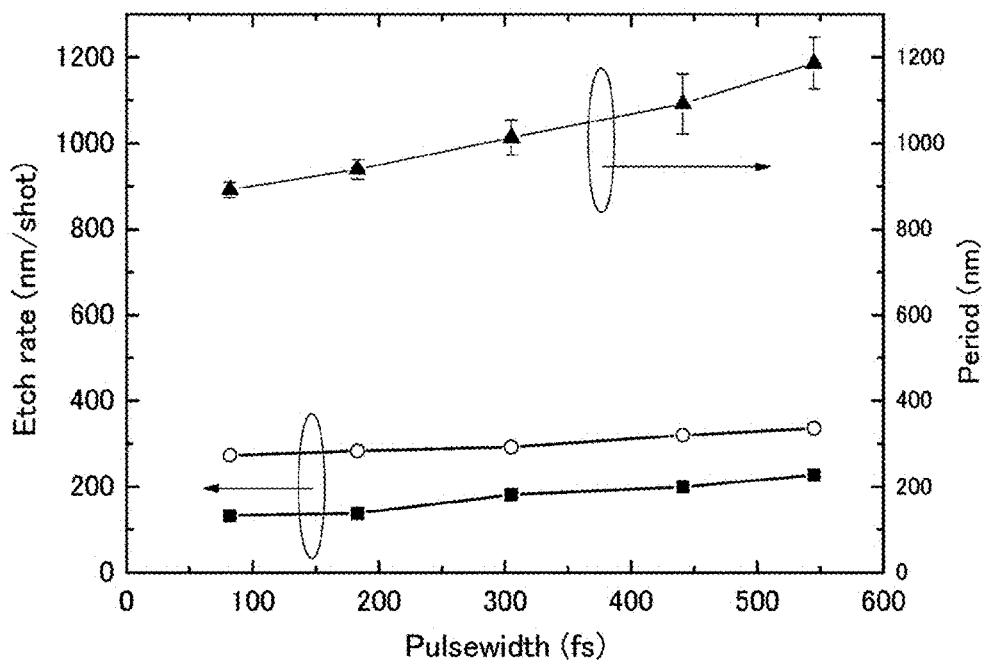

[FIG. 14]
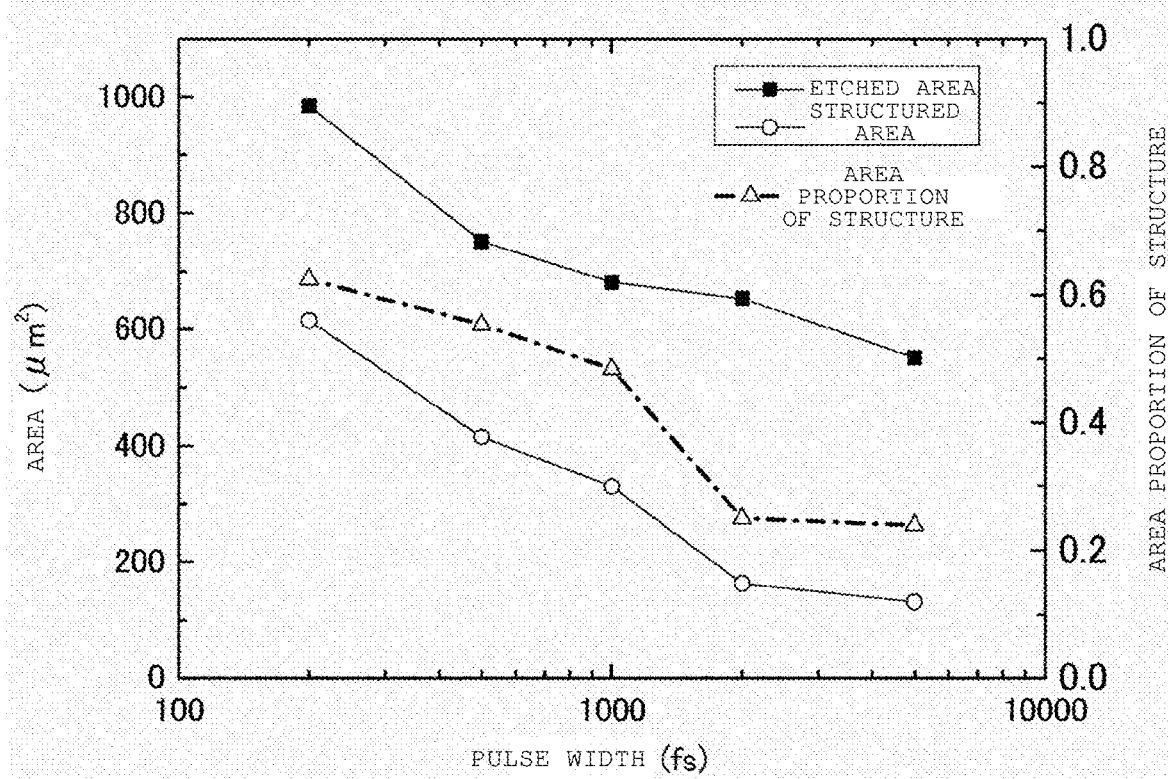
[FIG. 15]
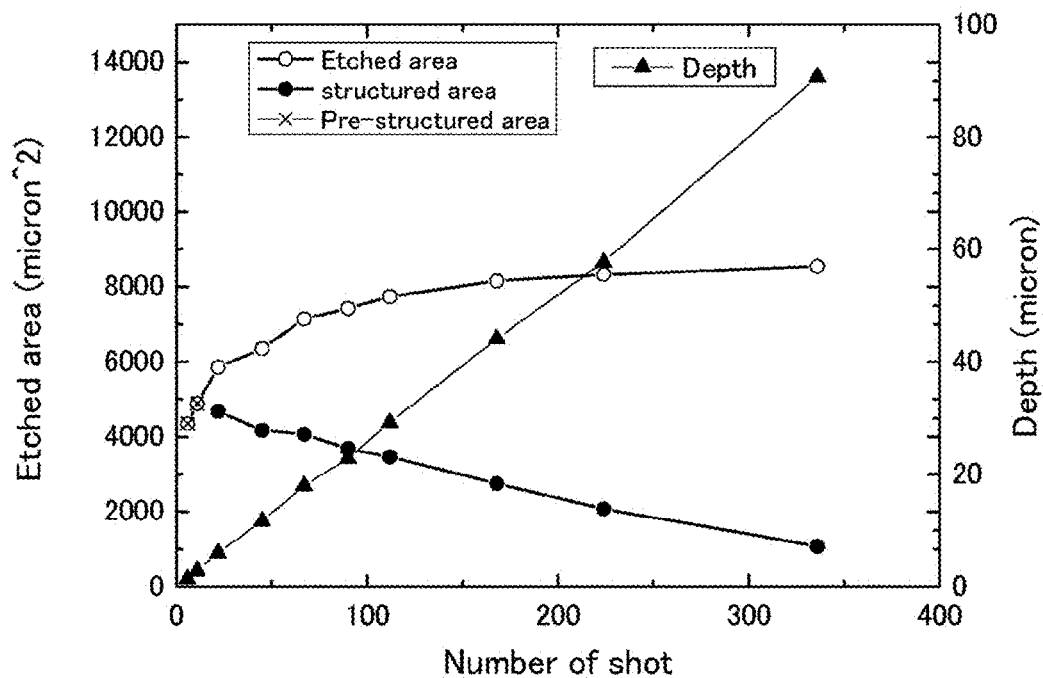

[FIG. 16]
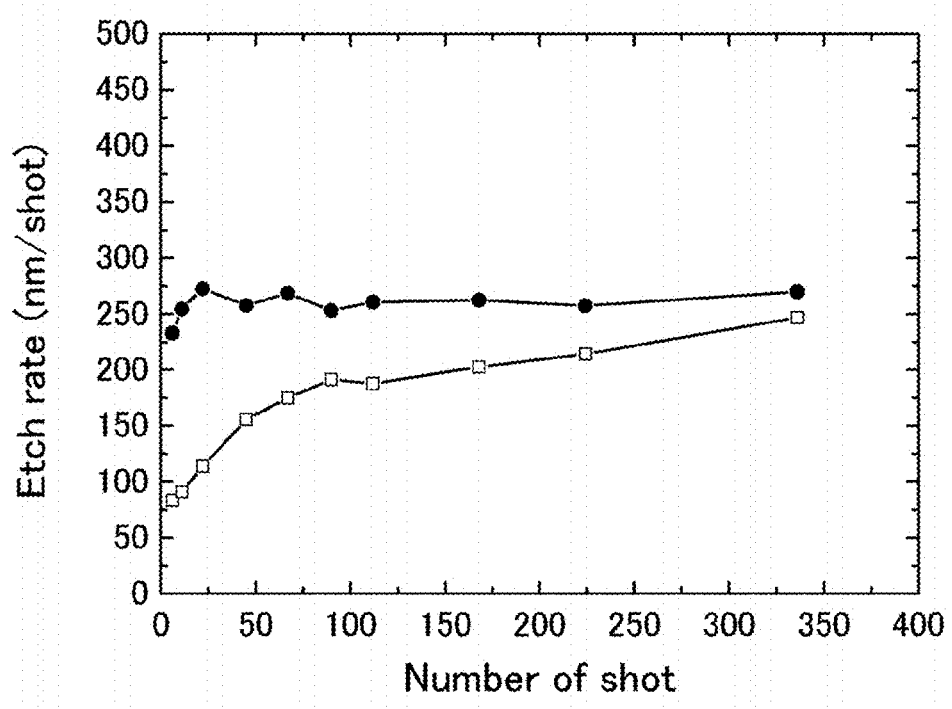
[FIG. 17]
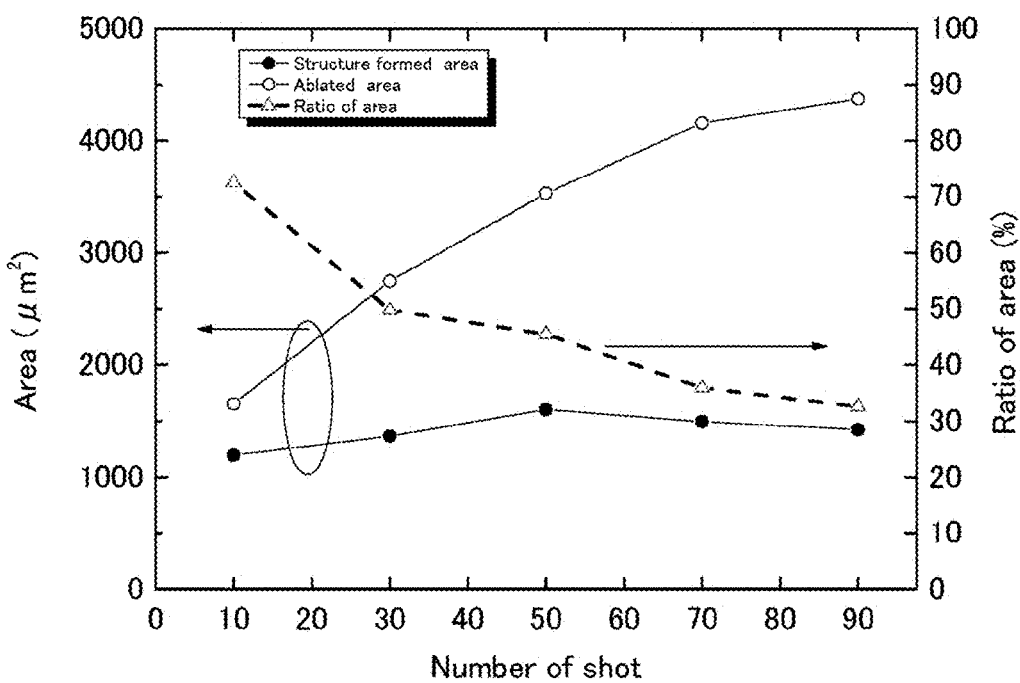

[FIG. 18]
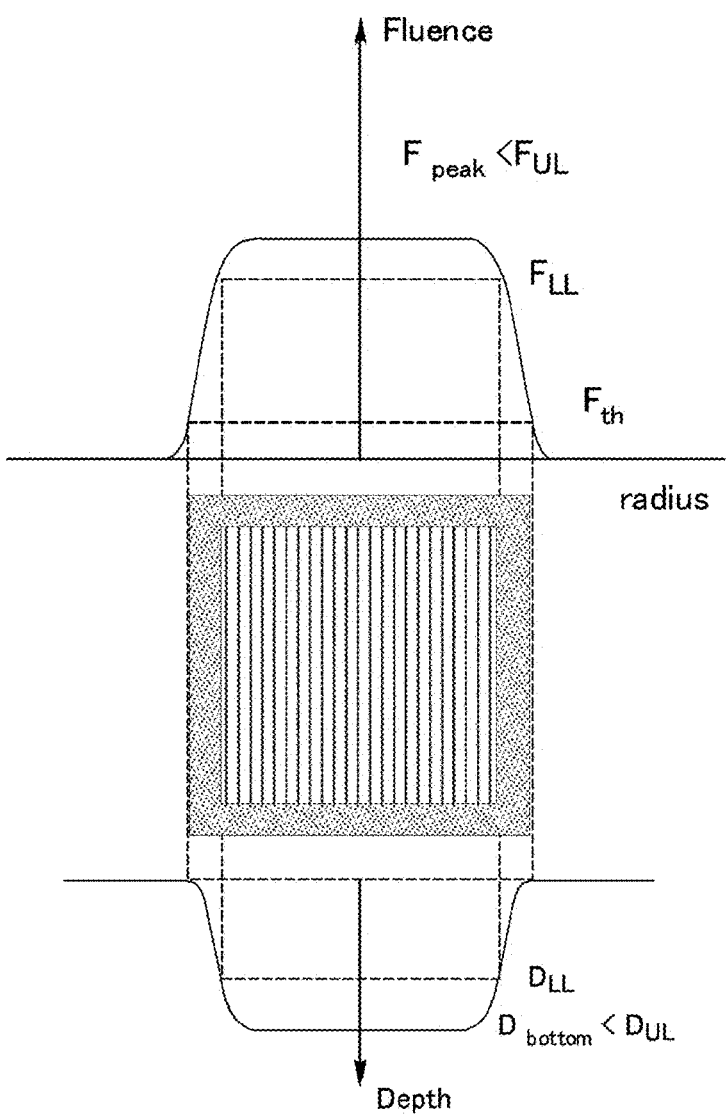

[FIG. 19]
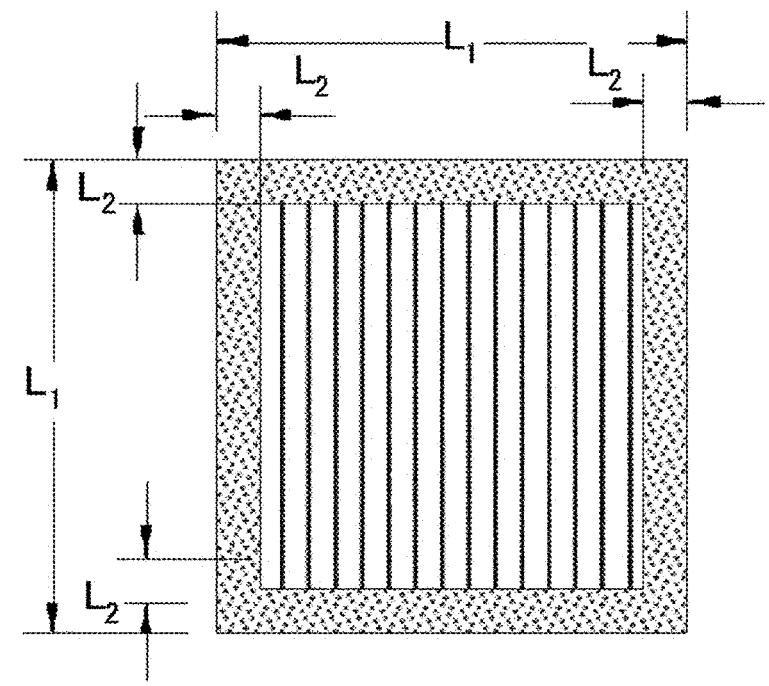
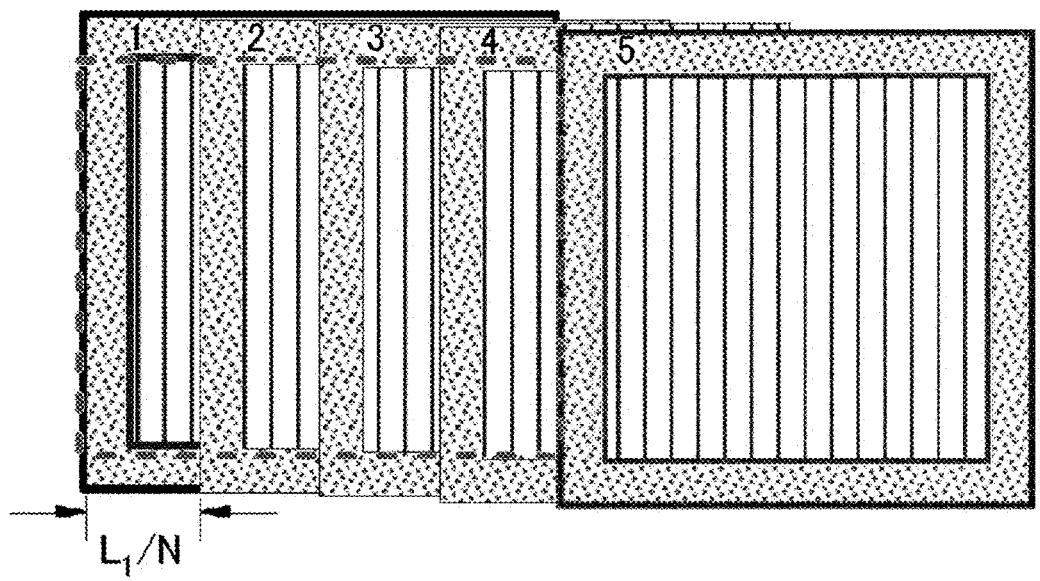

SURFACE STRUCTURE FORMING METHOD FOR ZIRCONIA-BASED CERAMICS, AND ZIRCONIA-BASED CERAMICS

TECHNICAL FIELD

The present invention relates to a surface structure forming method for fabricating a periodic microstructure on a surface of a zirconia-based ceramic, and to zirconia-based ceramics having a surface periodic structure.

BACKGROUND ART

There has been research and development of techniques that form a microstructured irregularities on a material surface. Formation of such a surface microstructure enables improving bonding to the overlying film, and adhesion for liquid, or altering the optical characteristics of the surface.

Zirconia-based ceramics, a material processed in this patent application, are known to have high-strength, and show characteristics that vary with the concentration and the type of additive. A material doped with a predetermined concentration of yttria (yttrium oxide) has toughness, and applications to biomaterials and machine materials are expected. This type of zirconia-based ceramic has also been used for oxygen sensors by taking advantage of the oxygen ion conducting property of the material.

Zirconia-based ceramics are not easily machineable because of mechanical characteristics such as toughness, hardness, and abrasion resistance. However, despite the poor workability, these desirable mechanical characteristics of zirconia-based ceramics have been exploited in biomaterial applications such as dental implants, and substitute bone. However, zirconia-based ceramics themselves have low compatibility to the body, and a technique that coats a highly biocompatible material such as apatite over the material surface is desired to improve biocompatibility. Materials containing tetragonal zirconia have desirable mechanical characteristics with no toxicity, and have been widely used as materials for medical equipment. Currently, these materials are used in a variety of practical applications, including artificial joints, dental restorations such as crowns, and artificial roots. However, tetragonal zirconia is inferior to calcium phosphate in terms of tissue conductivity, a property that encourages conduction of natural normal tissue to a material surface at the placement site. Because of this property, a thin fibrous connective tissue (with a thickness of 1 to 10 µm) occurs on a surface of the tetragonal zirconia placed in bone or soft tissue, and the material does not directly connect itself to the bone or soft tissue. It is also worth mentioning that, unlike calcium phosphate, there is no report of tetragonal zirconia in relation to blood compatibility. Accordingly, it would be useful to have a method that coats a surface of a ceramic material such as zirconia with a tissue conductive material to allow the material to directly connect itself to the bone in the body after operation. Calcium phosphates such as hydroxyapatite (a bone component) are considered to be most suited for the purpose of connecting a ceramic material to bone, and it has been proposed to coat a surface of a metallic material or a ceramic material such as zirconia with calcium phosphate to this end.

A prior art search for a method that improves adhesion for a film through formation of a microstructure on a surface of zirconia and other materials found the following techniques.

PTL 1 reports a nanolevel microprocessing technique whereby an ultrashort pulsed-laser (a femtosecond laser) is applied under polarization control to form a microstructure of a size smaller than the wavelength of the applied laser. A suitable fluence range is described as being from the ablation threshold to 10 times the ablation threshold. In this publication, "fluence" is described as energy per unit area ($J/cm^2$) determined by dividing the output energy per laser beam pulse by the cross sectional area of irradiation, and "ablation threshold" is described as the minimum value of energy density at which vaporization occurs on a material surface irradiated with a laser beam. PTL 1 reports that irradiation of a solid material surface with a linearly polarized ultrashort pulsed laser beam forms a narrow projecting microstructure along a direction orthogonal to the direction of polarization, and that irradiation of circularly polarized light forms a granularly projecting microstructure. The size of the microstructure has a positive correlation with the wavelength of the applied laser, and the microstructure has a size much smaller than the wavelength ($1/10$ to $3/5$ of the wavelength). As examples of surface microprocessing, PTL 1 uses a nitride ceramic (TiN) film, an amorphous carbon film, and a stainless steel material as samples.

PTL 2 reports a surface processing method that applies a single laser beam to a material surface to periodically form fine irregularities. In this patent, regions irradiated with a laser beam are scanned with an overlap, and ablation occurring at the interfering region of the p-polarized component of the incident light and the scattered light of the p-polarized component of along the material surface forms a self-organizing periodic structure orthogonal to the polarization direction of incident light, at an interval that is no smaller than the $\lambda/2$ of the incident light component and no greater than the incident light $\lambda$. The laser is described as being irradiated in 10 to 300 shots at a given region. PTL 2 takes advantage of the periodic structure that is formed in a direction orthogonal to the direction of polarization of incident light, and the direction of periodic structure is variable by varying the direction of polarization of incident light. A suitable fluence range is described as being in the vicinity of the ablation threshold. Surfaces of a Si substrate, a Cu tape, and an Al tape are examples of the samples worked in PTL 2.

PTL 3 proposes a method for fabricating a highly bone-compatible hydroxyapatite film on a silicon or stainless steel base material through vapor deposition of hydroxyapatite after fabricating periodic irregularities on a base material surface using an ultrashort pulsed-laser.

PTL 1 to PTL 3 are techniques that form periodic grooves in a direction orthogonal to the direction of polarization of incident light. There is no report of experiments conducted on zirconia-based ceramics.

In one of the few reports found by our prior art search for processing of zirconia-based ceramics with a femtosecond laser beam, NPL 1 describes direct ablation processing of dental implant zirconia on the order of several tens of micrometers, and evaluation of surface conditions after the process, and reports that the process has only a small effect on crystalline phase. There is no report of periodic structures of a submicron size.

A prior art search for the relationship between a direction of polarization of incident light and a microstructure found a report of periodic grooves formed in a $SiO_2$ material in a direction parallel to the direction of polarization of incident light (see NPL 2).

CITATION LIST

Patent Literature

PTL 1: JP-A-2003-211400
PTL 2: Japanese Patent No. 4054330
PTL 3: Japanese Patent No. 4440270

Non Patent Literature

NPL 1: R. A. Delgado-Ruiz et al., *Femtosecond laser microstructuring of zirconia dental implants*, Journal of Biomedical Materials Research B: Applied Biomaterials, VOL96B, ISSUE 1, pp. 91-100 (2011)
NPL 2: S. Hoehm, et al., *Femtosecond laser-induced periodic surface structures on silica*, J. Appl. Phys. 112 014901 (2012)

SUMMARY OF INVENTION

Technical Problem

As a way of improving base material surface adhesion for film coating, research and development is underway to make a microstructure on a base material surface. Some of the possible means of forming such a microstructure on zirconia-based ceramic include mechanical processing, processes that use a mediator such as sandblasting, and etching based on chemical reaction. However, there involve concerns of thermal adverse effects on material surface, and the influence of impurity doping. It is also not easy to make a submicron periodic structure on a structure formed by these techniques. It would accordingly be desirable to find a way to form a periodic microstructure of a submicron size on a zirconia-based ceramic surface without causing such adverse effects.

Previously methods of forming a microstructure on a metal surface was reported, such as etching that takes advantage of increase of light intensity due to interference of irradiated laser beams, and a formation of a periodic structure smaller than the wavelength by interference between scattered waves from surface and incident waves (see PTL 1 to PTL 3). The technique underlying PTL 2 and PTL 3 is that irradiation of a metal surface or a silicon surface with a laser beam of a fluence that causes ablation or damage forms irregularities with the size of the wavelength or half the wavelength on the solid surface (in a manner that depends on incident angle or refractive index). A microstructure of a size much smaller than the wavelength ($1/10$ to $3/5$ of the wavelength) is formed using different materials or different irradiate conditions. Specifically, the technique of PTL 1 forms periodic grooves in a direction orthogonal to the direction of polarization of incident light. Referring to PTL 2, the same phenomenon occurs across a range from a weak irradiation fluence in the vicinity of the ablation threshold to a high fluence, and a beam having a spatial Gaussian intensity distribution is continuously irradiated on different areas of a solid surface to form a periodic structure over a large area.

Previous reports of forming a microstructure by laser irradiation are reported for Si, metal, and TiN, as in PTL 1 to PTL 3, and there is no report of forming a periodic microstructure on zirconia-based ceramic.

For example, the method described in PTL 3 might be used to fabricate a solid surface structure with irregularities. The adverse effect of heat becomes an issue when the base material is a ceramic, particularly zirconia. Partially-stabilized zirconia undergoes volume changes due to a phase transition under heat. Such volume changes have a high risk of causing serious damage from the microstructure such as cracking and fracture. It is therefore important to find laser irradiation conditions that do not cause a phase transition while forming a periodic structure. In the techniques of the related art, the periodic irregularities are formed in a size that is no larger than the wavelength of a short pulsed laser, and many of the structures are smaller than submicron sizes because the wavelength of the laser used is on the order of microns, though the size depends on the laser wavelength. When solid fine particles as large as or larger than the period of the microstructure fly to the surface and adhere to the base material in the process of film deposition on the processed surface of the base material, the contact area with the film becomes smaller than a flat surface, irrespective of the irregularities. This results in a structure with poor adhesion.

The present invention is intended to find a solution to the foregoing problems. Accordingly, an object of the present invention is to provide a surface structure forming method that forms a periodic irregular microstructure on a zirconia-based ceramic surface. Another object of the present invention is to provide a zirconia-based ceramic having a periodic irregular microstructure. The period is desirably of a submicron to micron size (about 0.1 μm to 10 μm).

Solution to Problem

In order to achieve the foregoing objects, the present invention has the following features.

A method of the present invention is a surface structure forming method for zirconia-based ceramics, the method comprising irradiating a laser beam to a zirconia-based ceramic surface, and forming periodic irregularities in a spot of the laser beam irradiated.

A method of the present invention is a surface structure forming method for zirconia-based ceramics, the method comprising irradiating a linearly polarized ultrashort pulsed-laser beam to the ceramic surface, and forming stripe-pattern irregularities parallel to a direction of polarization of the linearly polarized light in a spot of the laser beam irradiated.

A method of the present invention is a surface structure forming method for zirconia-based ceramics, the method comprising irradiating a circularly polarized ultrashort pulsed-laser beam to the ceramic surface, and periodically forming a mesh-like raised region and a dot-like recessed region.

A method of the present invention is a surface structure forming method for zirconia-based ceramics, wherein the laser beam is focused to a spatial restricting mask of a shape that enables irradiating only a beam region that forms the periodic structure, and an image conforming to the shape is transferred to an optical system, and irradiated to the zirconia-based ceramic surface to lay down a plurality of periodic structure forming regions of said shape.

A zirconia-based ceramic of the present invention comprises periodic irregularities in a spot of a laser beam irradiated to a surface of the zirconia-based ceramic.

A zirconia-based ceramic of the present invention comprises a periodic irregularities of a parallel stripe pattern in a spot of a laser beam irradiation to a surface of the zirconia-based ceramic.

A zirconia-based ceramic of the present invention comprises a periodic structure with a mesh-like raised region and a dot-like recessed region in a spot of a laser beam applied to a surface of the zirconia-based ceramic.

Advantageous Effects of Invention

The present invention has achieved, for the first time, a zirconia-based ceramic having a periodic surface microstructure irregularities of a stripe pattern or a mesh-like raised pattern. Because the microstructure is formed by irradiating an ultrashort pulsed-laser beam, the microstructure can have irregularities of a period about the same as the wavelength of the laser used.

The zirconia-based ceramic having a surface microstructure of the present invention can be produced using an ultrashort pulsed-laser beam under appropriate conditions, and the surface is free from the adverse effect of heat, or the influence of impurity doping.

With the periodic microstructured irregularities, the adhesion for the film attached to the zirconia-based ceramic surface can improve, and the zirconia-based ceramic coated with such a film can have improved mechanical strength and heat resistance, in addition to the mechanical characteristics inherent to the zirconia-based ceramic.

The periodic microstructured irregularities can be formed over a large area, and a ceramic can be obtained that has a large ratio of a periodic structure region by irradiating a laser beam either continuously or using stamping.

With the fine irregularities, the zirconia-based ceramic having a periodic microstructure formed by using the method of the present invention can have improved adhesion for a calcium phosphate coating.

BRIEF DESCRIPTION OF DRAWINGS

FIG. 1 is a brief overview of the present invention, illustrating the direction of polarization of an incident laser beam on a workpiece, and the periodic structure formed on a surface of the workpiece, in which (a) represents a case where the laser beam is s-polarized light, (b) represents a case where the laser beam is p-polarized light.

FIG. 2 is a diagram explaining the relationship between the spatial distribution of laser beam irradiation (top), the surface structure distribution of a spot mark ablated by the laser beam (middle), and the depth distribution of the hole (bottom).

FIG. 3 is a schematic diagram explaining the periodic structure in the case of (a) linearly polarized light, and (b) circularly polarized light.

FIG. 4 is a schematic diagram showing a laser surface-processing device used in an embodiment.

FIG. 5 represents a photograph showing a laser beam irradiation mark in an embodiment of the invention, with arrows indicating the direction of polarization.

FIG. 6 is a diagram representing the relationship between etch rate and surface state after irradiating a linearly polarized laser beam.

FIG. 7 is a diagram representing the relationship between the peak fluence of a laser beam and etch rate after irradiating a laser beam.

FIG. 8 is a diagram representing the relationship between the peak fluence of a laser beam and surface state after irradiating a linearly polarized laser beam.

FIG. 9 is a diagram representing the relationship between etch rate and surface state after irradiating a linearly polarized laser beam.

FIG. 10 is a diagram representing the relationship between the state of a periodic structure, and incident angle after irradiating an s-polarized laser beam with incident angle θ.

FIG. 11 is a diagram representing the relationship between the state of a periodic structure, and incident angle after irradiating a p-polarized laser beam with incident angle θ.

FIG. 12 is a diagram representing the relationship between the pulse width of a laser beam, and the areas of ablated and periodically structured regions.

FIG. 13 is a diagram representing the relationship between the pulse width of a laser beam, etch rate, and the state of the periodic structure formed.

FIG. 14 is a diagram representing the relationship between the pulse width of a laser beam, and the areas of ablated and periodically structured regions.

FIG. 15 is a diagram representing the relationship between the number of shots of a laser beam, the area of a periodically structured region, and hole depth.

FIG. 16 is a diagram representing the relationship between the number of shots of a laser beam, and etch rate.

FIG. 17 is a diagram representing the relationship between the number of shots of a laser beam, the area of a processed region, the area of a periodically structured region, and the proportion of a region with the periodic structure.

FIG. 18 is a schematic view showing a square-shaped flat-top beam.

FIG. 19 represents a method for increasing the area of a periodic structure by scanning the flat-top beam.

DESCRIPTION OF EMBODIMENTS

Embodiments of the present invention are described below.

An embodiment of the present invention is concerned with a zirconia-based ceramic having a surface microstructure with stripe-pattern periodic irregularities, or a surface microstructure with a periodic pattern of a mesh-like raised region and a dot-like recessed region. The present invention is based on the novel finding that irradiating a laser beam on a surface of a zirconia-based ceramic forms a periodic microstructured irregularities in the laser irradiated spot. Specifically, the invention is based on the finding that irradiation of a linearly polarized laser beam forms a periodic microstructured irregularities of a stripe-pattern in a direction parallel to the direction of polarization, and that irradiation of a circularly polarized laser beam forms a periodic microstructure having a pattern of a mesh-like raised region and a dot-like recessed region.

The laser beam used in embodiments of the present invention is an ultrashort pulsed-laser that has only limited thermal effect in processes that form irregularities on a zirconia surface (a femtosecond laser that emits pulses within the time domain of femtoseconds; the laser includes a pulse width of 10 ps or less in embodiments of the present invention). A region irradiated with an ultrashort pulsed-laser undergoes changes in shape. However, the pulse energy as a whole can remain very low because of the high peak power, and the short pulse prevents the absorbed heat at the irradiated surface from diffusing into the surface or around the surface, allowing only the irradiated region to be blown off by ablation.

The laser beam used in embodiments of the present invention may be a known femtosecond laser such as titanium-sapphire lasers, and yttrium-doped lasers (within a time domain of femtoseconds (fs), and additionally 1 ps to 10 ps). It is also possible to use a wavelength tunable femtosecond pulse light source using a parametric amplifier based on a nonlinear wavelength conversion process.

Polarization includes linearly polarized light and circularly polarized light, or, more generally, elliptically polarized light. In embodiments of the present invention, a periodic microstructured irregularities of a stripe-pattern is formed in a direction parallel to the direction of polarization when the incident laser beam is linearly polarized light. In embodiments of the present invention, a periodic microstructured irregularities of a stripe-pattern is not formed when the incident laser beam is circularly polarized light, and a periodic microstructure having a pattern of a mesh-like raised region and a dot-like recessed region is formed instead.

When a linearly polarized laser beam is incident on a base material, a stripe-pattern periodic structure is formed in a direction parallel to the direction of polarization, regardless of whether the laser beam is s-polarized light that is perpendicular to the incident plane (a plane perpendicular to the reflecting surface and including the incident light), or p-polarized light that is parallel to the incident plane.

FIG. 1 is a brief overview of the present invention, illustrating the direction of polarization of an incident laser beam on a workpiece, and the periodic structure formed on a surface of the workpiece by laser irradiation. When the direction of polarization of the incident laser beam on the workpiece is s-polarized, the periodic irregularities on the surface of the zirconia-based ceramic has a stripe-pattern parallel to the direction of polarization (see FIG. 1, (a)). When the direction of polarization of the incident laser beam on the workpiece is p-polarized, the periodic irregularities on the surface of the zirconia-based ceramic has a stripe-pattern parallel to the direction of polarization (see FIG. 1, (b)). The symbol θ represents the incident angle of incident light.

FIG. 2 is a diagram explaining the relationship between the space distribution of laser beam irradiation (top), the surface structure distribution of a spot mark ablated by the laser beam (middle), and the depth distribution of the hole (bottom) in an embodiment of the present invention. The vertical axis in the top diagram represents fluence.

Fluence is described as energy per unit area of a pulse of a laser beam irradiated to a given region. In the case of a uniform beam, fluence is given as energy per unit area (J/cm$^2$) determined by dividing the output energy per laser beam pulse by the cross sectional area of irradiation. In the case of a spatially Gaussian beam, the peak fluence $F_{peak}$, which represents the maximum value at the beam center, is given by the following equation:

$$F_{peak}=2\cdot E/(\pi r^2),$$

where E is the pulse energy, and r is the beam radius at 1/e$^2$ intensity.

The vertical axis with a downward arrowhead in the lower diagram in FIG. 2 represents the depth distribution (Depth) of a hole. The depth distribution shows a shape after irradiation of certain shots of a laser pulse. The horizontal axis represents the radial distance of the spot. In FIG. 2(a) and FIG. 2(b), the vertical stripe pattern in the surface structure distribution shown in the middle represents a region with periodic irregularities. The outer dotted annular region represents a region where the ablation mark is present but lacking a distinct periodic structure. In the surface structure distribution shown in the middle of FIG. 2(b), the patchy pattern at the central region of the circle represents a region with a collapsed periodic structure.

In the diagrams, $F_{LL}$ represents the lower limits of an effective fluence range that forms a periodic structure. $F_{th}$ represents the ablation threshold of fluence that forms an ablation mark. $F_{UL}$ represents the upper limits of the fluence that forms a periodic structure. $D_{LL}$ represents the lower limits of the effective depth that forms a periodic structure in the hole. $D_{UL}$ represents the upper limits of the effective depth that forms a periodic structure in the hole.

FIG. 2(a) represents a case where $F_{peak}$ is smaller than $F_{UL}$. The hole depth is $D_{bottom}$ (depth to the bottom of the hole) $<D_{UL}$. FIG. 2(a) schematically illustrates that the periodic structure is indistinct in a region with a depth $0<D<D_{LL}$, and that the periodic structure is formed in a region with $D_{LL}<D<D_{bottom}$ (region with vertical stripes).

FIG. 2(b) shows a state after increasing the fluence from FIG. 2(a). FIG. 2(b) represents a case where $F_{peak}$ (the peak fluence intensity) is larger than $F_{UL}$. The hole depth is $D_{bottom}>D_{UL}$, where $D_{bottom}$ is the depth to the bottom of the hole. Referring to FIG. 2(b), increasing the fluence destroys the periodic structure at the central region of the hole in the laser spot, and makes a doughnut-shaped (cyclic) periodic structure region. The periodic structure is indistinct in a region where the hole depth D is $0<D<D_{LL}$. The region with $D_{LL}<D<D_{UL}$ (region with vertical stripes) is where a periodic structure is formed, and the region with $D_{UL}<D<D_{bottom}$ is a region where the periodic structure has collapsed because of the excessively high fluence.

Aside from the two states represented in FIG. 2, the peak fluence intensity can be $F_{th}<F_{peak}<F_{LL}$, or $F_{peak}<F_{LL}$. However, there will not be described because a periodic structure region will be absent in these cases.

FIG. 3 is a schematic diagram explaining the periodic structure, and the relationship between the period and the depth of the periodic structure in the case of linearly polarized light and circularly polarized light. FIG. 3(a) represents a case where incident light is linearly polarized light. FIG. 3(b) represents a case where incident light is circularly polarized light. In the case of circularly polarized light, recessed regions, shown in black, are periodically formed, and the raised regions have a mesh-like pattern. When incident light is linearly polarized light, the stripe period is about the same as the wavelength of the applied laser (about 0.9 to 1.3 times the wavelength). The stripe depth is less than about a half of the stripe period. When incident light is circularly polarized light, a structure with periodically arranged small holes and surrounding mesh-like raised regions is formed. Specifically, the structure has a shape with a mesh pattern, instead of stripes, and holes are formed that have a diameter about the same as the wavelength. The period is about the same as the wavelength of the applied laser (about 0.9 to 1.3 times the wavelength), as with the case of the linearly polarized light.

In order to form a microstructure having periodic irregularities, the ultrashort pulsed-laser is set so that the laser is irradiated several ten to several hundred pulses at the same position. These numbers are referred to as shots.

The states of the periodic structure to be formed (including the period, the area, and the proportion of the periodic structure) can be adjusted by appropriately setting parameters such as the type of laser beam (wavelength), the fluence of the laser beam, the number of shots, the etch rate (etching depth per unit shot), and the pulse width. The conditions for irradiating a laser beam to a workpiece and forming a fine periodic structure will be described in detail in the embodiments below. It is to be noted that the detailed descriptions of the embodiments below will be given through the case where incident light is linearly polarized light. However, the laser beam conditions for circularly polarized light are the same with the linearly polarized light case for controlling the periodic structure because the shape of the periodic structure formed by circularly polarized light develops into a mesh-like pattern (two-dimensional periodic structure) from the stripes pattern (one-dimensional periodic structure) formed by linearly polarized light.

The laser beam (wavelength) is preferably a titanium-sapphire laser (about 0.8 μm), or a yttrium-doped laser (about 1 μm), as noted above. Aside from these lasers, it is also possible to use an amplifier that utilizes the parametric wavelength conversion of a nonlinear optical process, or a light source involving wavelength conversion based on such a process. The wavelength is not particularly limited.

It has been found that a stripe-pattern periodic structure can be formed when the pulse width is within a domain of femtoseconds, and the pulse width may be about 10 fs to 10 ps. A pulse width of 500 fs or less is preferred because it makes it possible to make the area proportion of periodic structure 50% or more, even with a Gaussian beam. A pulse width of 100 fs or less is more preferred because an area proportion greater than 65% can be achieved in this pulse width range.

The periodic structure can be formed when the number of shots is about 12 or more and less than 400. The optimum shot range is about 20 to 70.

A stripe-pattern periodic structure always forms when the etch rate satisfies the condition that [etch rate/wavelength] is between 0.16 and 0.34.

In order to increase the area proportion of the periodic structure formed, it is preferable to use a beam of a uniform intensity distribution. As a method of achieving a uniform irradiation fluence, a laser beam maybe condensed through, for example, a pinhole to remove a region of laser beam that does not contribute to formation of a periodic structure, and the image through the pinhole may be transferred onto zirconia. In this way, the area of the periodic structure in the irradiated area can be increased.

The area of the periodic structure formed on a zirconia-based ceramic surface also can be increased in the following fashion. After forming a structure in the whole region of a location irradiated with a laser beam predetermined numbers of times, the laser is further irradiated over regions of the irradiated region, or to adjacent regions or to regions distant away from the irradiated region by moving the laser beam. By repeatedly forming the structure in this manner, large numbers of spot marks can combine together to increase the area of the periodic structure.

In an embodiment of the present invention, the zirconia-based ceramic may be, for example, a zirconia-based ceramic substrate, or a zirconia-based ceramic base material of a shape that is not limited to a plate shape. The zirconia-based ceramic includes base materials surface-coated with a zirconia film or zirconia-based ceramic.

In an embodiment of the present invention, the zirconia-based ceramic may be, for example, tetragonal zirconia. The zirconia-based ceramic may be a medical equipment material containing tetragonal zirconia. The medical equipment material containing tetragonal zirconia is a tetragonal zirconia-containing material used by being directly fixed in the body, or without being fixed in the body but in direct contact with body tissue or bodily fluid. Examples of the zirconia-based ceramic include a tetragonal zirconia polycrystal (TZP) that is 100% tetragonal zirconia, a partially-stabilized zirconia (PSZ) comprised of tetragonal zirconia and monoclinic crystalline zirconia, a zirconia toughened ceramic (ZTC) obtained by toughening a base material ceramic (e.g., $Al_2O_3$, SiC) with a unstabilized zirconia including tetragonal zirconia, a complex of tetragonal zirconia with metal zirconium or other metals by surface-coating or by dispersing. The stabilizer (e.g., CaO, MgO, $Y_2O_3$, $CeO_2$) used to stabilize tetragonal zirconia, and the content of such stabilizers are not particularly limited, as long as tetragonal crystals are stabilized.

The adhesion for a calcium phosphate coating can be improved when an adhesion layer of calcium phosphate fine particles smaller than the period of the irregularities is formed at a specific location on a surface of a medical equipment material containing a zirconia-based ceramic, for example, tetragonal zirconia, having the surface periodic structure described in the embodiment of the present invention.

First Embodiment

The present embodiment is described below with reference to FIGS. 4 and 5. FIG. 4 is a schematic diagram showing a laser surface-processing device used in the present embodiment. The device shown in FIG. 4 includes a laser source 1, a power control unit 2, a polarization control unit 3, a beam shaping unit 4, a condensing lens 5, and an irradiation stage 6. The power control unit 2 controls the power of a laser beam (unit: W), or the energy per pulse of a laser beam (unit: J). The polarization control unit 3 controls the direction of polarization of a laser beam and the state of the polarization, more specifically, linearly polarized light, elliptically polarized light, or circularly polarized light. The beam shaping unit 4 controls the beam shape, the intensity distribution inside of a beam, and the beam propagation direction. The irradiation stage 6 is a stage where a workpiece is mounted, and that is freely movable between positions (x, y, z, θ, ϕ) relative to a laser beam. The emitted laser beam from the laser source 1 is irradiated to a workpiece on the irradiation stage 6 via the device components, including the power control unit 2, the polarization control unit 3, the beam shaping unit 4, and the condensing lens 5, in order.

Irradiating a linearly polarized laser beam (titanium-sapphire, or simply "TiS"; a wavelength of about 0.8 microns, a pulse width of 80 fs) to a zirconia-based ceramic surface formed a fine periodic structure of irregularities having a parallel stripe pattern. The direction of polarization of the linearly polarized laser beam was parallel to the stripes. The periodic structure had a period of about 948 nm/cycle, on average. The periodic structure had about the same or a slightly longer than the wavelength of the applied laser beam. A laser microscopy observation revealed that the structure had a depth of 350 to 400 nm (from the bottom to the top of the irregularities). The depth was about ⅓ to ½ of the period.

FIG. 5 shows a laser micrograph after irradiation of a linearly polarized laser beam. The arrow indicates the direction of polarization of the linearly polarized light. As can be seen, the laser irradiation mark includes irregularities with a vertical stripe pattern parallel to the direction of polarization of the linearly polarized light, and an annular ablation mark with indistinct stripes surrounding the periodic structure. FIG. 5 corresponds to the diagram of ablated surface distribution shown in the middle of FIG. 2(a).

Irradiating a circularly polarized laser beam (TiS; a wavelength of about 0.8 microns, a pulse width of 80 fs) to a zirconia-based ceramic surface created a laser irradiation mark with a mesh-like raised region, rather than stripes. Specifically, a periodic structure of a mesh-like shape, rather than stripes, appeared, and an annular ablation mark with indistinct mesh-like patterns was confirmed around the periodic structure.

The change of the crystalline phase of the zirconia-based ceramic surface having the surface microstructure was observed before and after the process. A crystalline phase change (a change from tetragonal crystals to monoclinic crystals) was 2% or less as observed by Raman microscopy and X-ray diffraction. The result confirmed that the surface had hardly any adverse effect, thermally or mechanically.

When a linearly polarized laser beam (TiS; a wavelength of about 0.8 microns, a pulse width of 80 fs) was irradiated by being continuously scanned or moved, a periodic structure of a parallel stripe pattern parallel to the direction of polarization was obtained just in the final irradiation spot mark upon stopping (ending) the scan. The result confirmed that the stripe pattern direction was dependent on the direction of polarization, not on the scan direction. An annular ablation mark with no periodic structure was formed at the peripheral regions surrounding the periodic structure at the central region of the irradiation spot mark, and a collapsed periodic structure was observed in the scanned region.

In the case of a zirconia-based ceramic, a periodic structure is formed at a fluence at or above a certain threshold, however, the Gaussian beam includes a fluence region where the fluence is at or below the threshold and at or above the ablation threshold. It was confirmed that the periodic structure is destroyed by passing of such a low fluence region, when irradiating a laser beam of a Gaussian intensity distribution with continuously moving the laser beam.

Second Embodiment

A laser source different from that used in First Embodiment was used in the present embodiment. Irradiating a linearly polarized laser beam (Yb-doped KGW (KGd(WO$_4$)$_2$; a wavelength of 1.03 microns, a pulse width of 200 fs) on a zirconia-based ceramic surface formed a periodic microstructured irregularities of a parallel stripe pattern on the surface. The laser beam was irradiated 50 shots. The direction of polarization of the linearly polarized laser beam was parallel to the stripes. The periodic structure had a period of about 1.05 μm/cycle, on average. The period observed had about the same or a slightly longer than the wavelength of the irradiated laser beam. The surface structure was similar to that obtained in First Embodiment, despite the different laser source.

Third Embodiment

The present embodiment is described with reference to FIGS. 6, 7, and 8. The present embodiment describes the optimum conditions for forming the periodic structure, among others.

The etch rate refers to the depth D of an etched hole per shot of a laser beam. In the embodiment, depth D is the mean value determined by, for example, dividing the depth of a hole by the number of shots, 40, irradiated to form the hole. The unit is nm/shot. Here, the shot in the denominator means that the depth is the average value per unit shot.

FIG. 6 is a diagram representing the relationship between etch rate and a surface state, for example, the presence or absence of a stripe-pattern surface periodic structure, after 40 shots of a linearly polarized laser beam (TiS; a wavelength of 810 nm, 80 fs). In the figure, the horizontal axis represents the etch rate (unit: nm/shot), and the vertical axis represents the state of a laser spot mark in four levels: "No mark", "No periodic structure (with a mark)", "Periodic structure", and "Collapsed periodic structure". Z is a value relating to the distance between the condensing lens and the zirconia. The zirconia is closer to the focal point of the laser, and the fluence is higher when Z=4 mm than when Z=0 mm. Solid squares indicate Z=0 mm (focused beam diameter=124 microns), solid circles indicate Z=4 mm (focused beam diameter=95 microns), and blank circles indicate internal observation at Z=4 mm. Here, "internal observation" means an observation made to estimate the borderline of structure formation, whereby a region inside the beam that forms a structure is observed, and the etch rate forming a structure is sorted from the upper limit and the lower limit of the hole depth forming the structure.

"A collapsed periodic structure" refers to when the periodic structure collapses from a high fluence region (the beam center in the case of a Gaussian beam), and the periodic structure is in the annular region. It can be seen from the diagram that a stripe-pattern periodic structure always forms when the etch rate is between 132 and 280 (nm/shot). Each dot in the diagram represents the result of experiments conducted under different peak fluence conditions (states), and the etch rate was varied by varying the pulse energy of the irradiated laser.

FIG. 7 is a diagram representing the relationship between the peak fluence of a laser beam, and etch rate after irradiating a laser beam (TiS; a wavelength of 810 nm), 80 fs, 40 shots). Circles indicate Z=0 mm (focused beam diameter=124 microns), and triangles indicate Z=4 mm (focused beam diameter=95 microns). As shown in the diagram, the etch rate and the peak fluence $F_{peak}$ (logarithm) are related to each other. From the relationship between the peak fluence of a laser beam and the etch rate shown in FIG. 7, a corresponding peak fluence of the etch rate can be determined for given irradiation conditions (laser wavelength, pulse width, repeating rate). Conversely, a corresponding etch rate can be determined from the peak fluence.

FIG. 8 is a diagram representing the relationship between the peak fluence of a laser beam, and a surface state, for example, the presence or absence of a stripe-pattern surface periodic structure, after 40 shots of a linearly polarized laser beam (TiS; a wavelength of 810 nm, 80 fs). In the figure, the horizontal axis represents the peak fluence (unit: J/cm$^2$), and the vertical axis represents the state of a laser spot mark in four levels: "No mark", "No periodic structure (with a mark)", "Periodic structure", and "Collapsed periodic structure (collapse from the center)". Solid squares indicate Z=0 mm, and blank circles indicate Z=4 mm. It can be seen from the diagram that a stripe-pattern periodic structure always forms when the peak fluence is between 2.7 and 7.7 (J/cm$^2$). The peak fluence at the boundary between "No mark" and "No periodic structure (with a mark)" corresponds to the ablation threshold. In the diagram, the ablation threshold is about 2 (J/cm$^2$).

Fourth Embodiment

The present embodiment is described with reference to FIG. 9. The present embodiment describes the optimum conditions for forming a stripe-pattern periodic structure as in Third Embodiment but with a laser beam of a different wavelength from Third Embodiment.

FIG. 9 is a diagram representing the relationship between the etch rate of a laser beam, and a surface state, for example, the presence or absence of a stripe-pattern surface periodic structure, after irradiating a linearly polarized laser beam (Yb-doped KGW; a wavelength of 1.03 microns, 200 fs). In the figure, the horizontal axis represents the etch rate (unit: nm/shot), and the vertical axis represents the state of a laser spot mark in four levels: "No mark", "No periodic structure (with a mark)", "Periodic structure", and "Collapsed periodic structure". "A collapsed periodic structure" refers to when the periodic structure collapses from the center, and the periodic structure is in the annular region. As shown in the insert at the bottom right corner of the diagram, the structure was fabricated at different fluences by varying the laser pulse energy and the irradiation area. Squares indicate a pulse energy of 28 µJ, circles indicate a pulse energy of 60 µJ, triangles indicate a pulse energy of 110 µJ, inverted triangles indicate a pulse energy of 144 µJ, diamonds indicate a pulse energy of 186 µJ, left-pointing triangles indicate a pulse energy of 222 µJ, and right-pointing triangles indicate a pulse energy of 272 µJ. As shown in the diagram, it was found that a stripe-pattern periodic structure always forms when the etch rate is between about 158 and about 355 (nm/shot). A periodic structure always formed when the peak fluence was 1.5 to 5.0 (J/cm$^2$). The ablation threshold was about 1.2 (J/cm$^2$).

From the result that the periodic structure was formed with at least several shots of a laser beam, one of the conditions limiting the formation of the periodic structure is that the etch rate does not exceed the stripe depth. Judging from the embodiment, the lower limit of etch rate is at least 1/5 of the stripe depth. In terms of the stripe period, the etch rate is 1/10 to 1/2 of the stripe period. In order to form a distinct periodic structure, the etch rate is desirably 1/5 to 1/2.5 of the stripe depth.

From Third and Fourth Embodiments, [etch rate/wavelength] is 132 to 280 (nm/shot)/810 nm=0.16 to 0.34 in Third Examples, and 158 to 355 (nm/shot)/1,030 nm=0.15 to 0.34 in Fourth Embodiment. It can be said from these results that a stripe-pattern periodic structure can be reliably formed when [etch rate/wavelength] is 0.16 to 0.34, even when the wavelength of the femtosecond laser beam is different.

Fifth Embodiment

The present embodiment is described with reference to FIGS. 10 and 11. In the present embodiment, the relationship between the incident angle of a laser beam, and the stripe-pattern periodic structure was examined.

FIG. 10 is a diagram representing the relationship between the state of a periodic structure, and incident angle after an s-polarized laser beam (a center wavelength of 810 nm, a pulse width of about 80 fs) is incident on a zirconia-based ceramic substrate with incident angle θ. The horizontal axis represents the incident angle θ (deg), and the vertical axis represents the period (unit: nm) of the stripe-pattern periodic structure formed. The period of the stripe-pattern ranges from about 840 to 900 nm, and the period change against incident angle θ falls within the data variation range, suggesting that the period is not dependent on incident angle.

FIG. 11 is a diagram representing the relationship between the state of a periodic structure, and incident angle after a p-polarized laser beam (a center wavelength of 810 nm, a pulse width of about 80 fs) is incident on a zirconia-based ceramic substrate with incident angle θ. The horizontal axis represents the incident angle θ (deg), and the vertical axis represents the period (unit: nm) of the stripe-pattern periodic structure formed. The period of the stripe-pattern ranges from about 900 to 1,040 nm, and the period has a tendency to increase with increase of incident angle θ in the case of p-polarized light. However, the angle dependence is not large also in p-polarized light.

The results observed in the present invention differ from the previously reported angle dependence of a periodic structure orthogonal to the polarization (e.g., PTL 2), both for p-polarized light and s-polarized light.

Sixth Embodiment

The present embodiment is described with reference to FIGS. 12 and 13. In the present embodiment, the relationship between the pulse width of a laser beam, and the periodic structure of stripe patterns was examined. For the examination, the present embodiment used a TiS laser beam (a center wavelength of 810 nm) with 40 shots irradiation.

FIG. 12 is a diagram representing the relationship between the pulse width of a laser beam, and the areas of ablated and periodically structured regions. The horizontal axis represents the pulse width (unit: fs), and the vertical axis represents the area (left; unit: µm$^2$), and the area ratio of a periodic structure region with respect to the total area of the hole at a laser irradiation mark (right; unit: %). Measurements were made by varying the pulse width of a laser beam from about 80 to 600 fs. Formation of a stripe-pattern periodic structure was confirmed at the all measured pulse widths up to 600 fs. With a laser beam applied in a pulse width of 80 fs at the optimum fluence of 6.4 J/cm$^2$, the hole area and the area of the periodically structured region had a tendency to decrease|[A1]|[A2] as the pulse width increased. In the diagram, blank circles with solid lines represent the area of a laser-induced hole, and solid circles with thick lines represent the area of a region with a stripe-pattern periodic structure. In the diagram, dashed-dotted lines represent the area ratio of a periodic structure region with respect to the total area of the hole at a laser irradiation mark (unit: %). The ratio had a tendency to decrease as the pulse width increased. It can be seen from the figure that shorter pulse widths are preferred. The fluence was constant in the examination shown in the figure. However, the upper limit of pulse width is not limited to 1 picosecond when the fluence is appropriately optimized for the pulse width.

FIG. 13 is a diagram representing the relationship between the pulse width of a TiS laser beam (a center wavelength of 810 nm, 40 shots), etch rate, and the state of the periodic structure formed. The horizontal axis represents the pulse width (unit: fs), and the vertical axis represents the etch rate (left; unit: nm/shot), and the period of the stripe-pattern periodic structure (right; unit: nm). Measurements were made by varying the pulse width of a laser beam from about 80 to 600 fs. Formation of a periodic structure was confirmed at the all measured pulse widths up to 600 fs. In forming a structure with a pulse width of 80 fs at the optimum fluence of 6.4 J/cm$^2$, the etch rate had a tendency to increase as the pulse width increased. The period of the periodic structure also had a tendency to increase as the pulse width increased. Blank circles with solid lines represent "the etch rate at the center of a laser beam", solid squares with solid lines represent "the lower limits of the etch rate in a region of a laser beam that formed a stripe-pattern periodic structure". The etch rate at the peak fluence can be represented by etch rate (peak fluence)=$D_{bottom}$/shot. "The lower limit of the etch rate in a region of a beam that formed a stripe-pattern periodic structure" can be represented by etch rate (lower limit)=$D_{LL}$/shot. Solid triangles with solid lines represent the period of stripe patterns. The period was about 900 to 1,200 nm for a pulse width of 80 to 550 fs. The etch rate (at the peak fluence) and the etch rate (at the lower limit) become closer to each other as the pulse width increases. This means narrowing of the region with a periodic structure.

It was found that the stripe-pattern periodic structure can be formed when the pulse width is within a domain of femtoseconds, and a pulse width of about 10 fs to 10 ps is usable. A pulse width of 500 fs or less is preferred because it makes it possible to make the area proportion of periodic structure 50% or more, even with a Gaussian beam. A pulse width of 100 fs or less is even more preferred because an area proportion greater than 65% can be achieved in this pulse width range.

Seventh Embodiment

The present embodiment is described with reference to FIG. 14. In the present embodiment, the relationship between the pulse width of a laser beam, and the periodic structure of stripe patterns was examined using an Yb-based laser beam (a center wavelength of 1.03 µm).

A 1.03-µm Yb laser was irradiated on a zirconia-based ceramic with 20 shots per location at a peak fluence of 4 J/cm$^2$ with a repetition frequency of 15 kHz. The laser pulses with pulse widths of 200 fs, 500 fs, 1 ps, 2 ps, and 5 ps, were irradiated and the formation of a periodic structure on the bottom surface was confirmed.

FIG. 14 is a diagram representing the relationship between the pulse width of a laser beam, and the areas of ablated and periodically structured regions. The horizontal axis represents the pulse width (unit: fs), and the vertical axis represents the area (left; unit: µm$^2$), and the area ratio of a periodic structure region with respect to the total area of the hole at a laser irradiation mark (right; "area proportion of structure"). Measurements were made by varying the pulse width of a laser beam from about 200 fs to 5 ps. Formation of a stripe-pattern periodic structure was confirmed at all measured pulse widths up to 5 ps. The are area of the formed hole, and the area of the periodically structured region had a tendency to decrease as the pulse width increased. In the diagram, solid squares with solid lines represent the laser-induced hole area ("etched area"), and the blank circles with solid lines represent the area of a region with the stripe-pattern periodic structure. In the diagram, triangles with dashed-dotted lines represent the area ratio of a periodic structure region with respect to the total area of the hole at a laser irradiation mark. The ratio had a tendency to decrease as the pulse width increased. It can be seen from the figure that shorter pulse widths are preferred for efficient formation of the periodic structure.

The relationship between pulse width, etch rate, and the state of a periodic structure was also examined. Measurements were made by varying the pulse width of a laser beam from about 200 fs to 5 ps. The etch rate had a tendency to increase as the pulse width increased. The period of the periodic structure also became more likely to increase as the pulse width increased. The period was about 1,000 to 1,400 nm for the pulse width of about 200 fs to 5 ps. The peak fluence, etch rate and the lower limit of etch rate become closer to each other as the pulse width increases. This means narrowing of the region with a periodic structure.

Eighth Embodiment

The present embodiment is described with reference to FIGS. 15 and 16. In the present embodiment, the relationship between the number of shots of a laser beam, and the stripe-pattern periodic structure was examined. For the examination, the present embodiment used a TiS laser beam (a center wavelength of 810 nm, a pulse width of 80 fs). The fluence was 6.6 J/cm$^2$.

FIG. 15 is a diagram representing the relationship between the number of shots of a laser beam, the area of a periodically structured region, and hole depth. The horizontal axis represents the number of shots, and the vertical axis represents the area of a periodic structure (left; unit: µm$^2$), and the hole depth (right; unit: microns). Measurements were made with about 6 to 340 shots of a laser beam. The periodic structure was indistinct between 6 and 11 shots ("pre-structured"; indicated by × in the diagram). The periodic structure was distinct in data for 22 shots. In the figure, blank circles with solid lines represent the etched area, solid circles with solid lines represent the area of a periodically structured stripe-pattern region, and solid triangles with solid lines represent the hole depth. The processed area, and the hole depth increased with increasing numbers of shots. However, the area of a periodically structured stripe-pattern region had a tendency to decrease. Formation of a periodic structure was confirmed up to 340 shots. Extrapolation of the data in the diagram suggests that the hole becomes deeper, and the periodic structure will not be formed at the bottom surface when the number of shots is 400 or more, or the bottom surface will not be flat. Referring to the figure, the stripe-pattern periodic structure can be obtained with any number of shots in a range of 12 or more and less than 400. It can be seen from the figure that fewer shots are desirable, provided that a distinct periodic structure is formed. The optimum range is preferably about 20 to 70 shots.

FIG. 16 is a diagram representing the relationship between the number of shots of a laser beam, and etch rate (unit: nm/shot). The horizontal axis represents the number of shots, and the vertical axis represents the etch rate. Measurements were made with about 6 to 340 shots of a laser beam. Solid circles with solid lines represent "the etch rate at the center of a laser beam", blank squares with solid lines represent "the lower limits of the etch rate in a region of a laser beam that formed a stripe-pattern periodic structure". In the diagram, the region of etch rate above the blank squares with solid lines, and below the solid circles with solid lines represents a region where the values of etch rate are appropriate for the formation of the periodic structure. It can be seen that the numerical range of etch rate that forms the periodic structure becomes narrower as the number of shots increases.

Ninth Embodiment

The present embodiment is described with reference to FIG. 17. In the present embodiment, the relationship between the number of shots and the stripe-pattern periodic structure was examined using a laser beam of a different wavelength from Eighth Embodiment. For the examination, the present embodiment used an Yb-doped KGW laser beam (a center wavelength of about 1 micron, a pulse width of 200 fs).

FIG. 17 is a diagram representing the relationship between the number of shots of a laser beam, the area of a periodically structured region, and the proportion of a periodic structure region with respect to the whole processed region. The horizontal axis represents the number of shots, and the vertical axis represents the area of a periodic structure (left; unit: µm$^2$), and the proportion of a periodic structure region with respect to the whole processed region (right; unit: %). Measurements were made with about 10 to 90 shots of a laser beam. Solid circles with solid lines represent the area of a region with a stripe-pattern periodic structure, blank circles with solid lines represent the total area of an ablated region, and triangles with dotted lines represent the proportion of a periodic structure region with respect to the whole processed region. Formation of a stripe-pattern periodic structure was confirmed with 10 shots. The stripe-pattern periodic structure had the largest area with 50 shots. The peripheral region where only ablation occurs with no formation of a periodic structure increases as the number of shots is increased further. The proportion of a periodic structure region with respect to the whole processed region becomes smaller as the number of shots is increased. Referring to the figure, the optimum number of shots is 50 from the standpoint of forming a distinct periodic structure, and increasing the area of the structure region. It can be seen that the three largest areas occur with 50, 70, and 90 shots, and the three largest proportions of a region with a distinct period occur with 30, 50, and 70 shots. Referring to the figure, the stripe-pattern periodic structure can be obtained with any number of shots between 10 and 90 shots. However, the optimum number of shots is between about 30 and 70 shots.

Tenth Embodiment

The foregoing measurements are based on the formation and the processes using a zirconia-based ceramic, specifically 3 mol % $Y_2O_3$ zirconia. However, it was confirmed that other compositions produce the similar results. Zirconia ceramics containing 4 mol %, 8 mol %, and 10 mol % $Y_2O_3$ (will be called 4Y, 8Y, and 10Y, respectively), and a zirconia containing 3 mol % $Y_2O_3$, and 20% $Al_2O_3$ (will be called 3Y20A) were irradiated with a linearly polarized laser beam (a center wavelength of 810 nm, a pulse width of 100 fs, a repetition frequency of 560 Hz), which was applied in 40 shots at a peak fluence of 6.9 J/cm². A stripe-pattern periodic structure parallel to the direction of polarization of the linearly polarized light was observed in all cases. The period of the observed structure was about 900 nm to 910 nm for 4Y, 8Y, and 10Y. The period was about 940 nm for 3Y20A. The etch rate showed a tendency to increase in order from 3Y, 4Y, 8Y, 10Y, and 3Y20A.

Metal was examined as material of the workpiece of surface process. A zirconia surface was partially coated with metal (Al), and a linearly polarized laser beam was irradiated in the same manner as in the embodiment. This formed stripes on the metal surface in a direction perpendicular to the direction of polarization, as opposed to the stripes formed in a direction parallel to the polarization on a zirconia surface. It can be seen from this that the present embodiment is a method that is effective for processing of zirconia-based ceramics.

Eleventh Embodiment

The present embodiment describes irradiation of a laser beam with an optical element that creates a uniform beam intensity distribution in a laser surface-processing device.

The spatial distribution of the irradiated laser beam takes the form of a Gaussian distribution, as shown in FIG. 2. However, when a laser beam is irradiated that has a uniform beam intensity distribution created with the use of an optical element that forms a uniform beam intensity distribution, the hole depth became substantially uniform at the irradiated region, and the periodic structure was formed in 90% or higher percentages of the ablated bottom surface.

Twelfth Embodiment

The present embodiment describes a method for increasing the area of the stripe-pattern periodic structure.

In an observation of a case of a continuous scan of a laser beam, the periodic structure was destroyed at the skirts of the beam. In a continuous scan of a laser beam performed in the manner described in the related art, the periodic structure will not be observed in the continuously moving regions of the beam. However, the periodic structure was observed at the central region of the spot where the beam was stationary. The result was the same for a laser beam scan direction parallel to the direction of a linearly polarized laser beam, and for a laser beam scan direction orthogonal to the direction of a linearly polarized laser beam. This is because, when the laser beam is irradiated in about 40 shots per location, the amount of shift of the irradiation position is smaller than the length at which the structure is destroyed by the skirt of the beam.

The periodic structure can be fabricated by scanning when an optical system is used that shapes the laser beam to have a flat-top intensity profile. For a flat-top laser beam, the scanning method is suitable if the required number of shots is small, or the beam size is large.

While a large-area structure can be formed by scanning using an ideal flat-top beam, however, because the actual beam has a weak intensity region of a finite width the area proportion of the periodic structure formed by scanning method becomes small in forming a periodic structure that requires multiple shots. FIG. 18 shows a simplified, square-shaped flat-top laser beam. FIG. 19 represents a method for increasing the area of a periodic structure by scanning the flat-top beam. Referring to FIG. 19, the following considers a case where the beam is applied by being moved shot by shot from the left to right (scan irradiation). The vertical stripes in the figure represent a region with a periodic structure, and the surrounding area is an ablated region with no periodic structure. As an example, the beam needs to be applied in N shots in a given location, and $C_1=L_2/L_1$, where $L_1$ is the ablated length along the scan direction, and $L_2$ is the length on either side of end regions where the structure is not formed. When equivalently irradiating the beam in N shots in one location while continuously scanning the irradiation site, the beam has a shift per shot of $L_1/N$, and the length of the horizontal direction with a periodic structure is given by $L_3=(L_1/N)-L_2$. The structure remains when $L_3$ is positive, whereas the structure collapses at the shoulders of the scanned beam when $L_3$ is negative.

In terms of the region surrounded by dotted lines in FIG. 19 (shots 2, 3, and 4 overlying shot 1), the proportion of the horizontal region with the structure is given by $R_{area}=1-N*C_1$. For example, when $C_1=0.1$, $R_{area}$ becomes 0.6 upon scanning with 4 shots of a laser beam at a given location (N=4), and the structure remains in 60% of the horizontal direction. The proportion of the structure in the total area becomes 48% when the effect of vertical shoulders is taken into account.

It is preferable to have larger values of $L_1$, and smaller values of $L_2$ and N to satisfy the condition $L_3>0$. The magnitude of $L_1$ is determined by the laser power, whereas $L_2$ is determined by the uniformity and the shape of the beam. N is dependent on the fluence and the pulse width of the laser.

In order to form a periodic structure over a wide area of a zirconia base material surface, a laser beam is scanned spot by spot, either continuously or discontinuously. Here, scanning of a laser beam spot by spot means, for example, making a structure by repeating the procedure that includes forming a structure in the whole region of a location irradiated more than once or predetermined numbers of times with a Gaussian beam or a beam having a uniform intensity distribution, or with a beam that has been adjusted to have a uniform intensity distribution, and further irradiating the laser beam over regions of the irradiated region, or to adjacent regions or to regions distant away from the irradiated region by moving the laser beam. Application of a laser beam to adjacent regions or to regions distant away from the irradiated region is also referred to as stamping or stepped application. Application of a laser beam with some overlap is essentially continuous scanning.

A linearly polarized laser beam was adjusted to have a wide uniform distribution, and irradiated to one location in 40 shots. The laser beam was then moved over a distance that was at least the length of the spot size, and irradiated to a location that had no overlap with the previous spot. A device with a system of lenses configured to create a spatially uniform beam, and a slit of a variable vertical and horizontal aperture size were used to select a uniform spatial intensity distribution, and this image was transferred to an irradiation site using an imaging optical system. The beam was irradiated over a 10 mm×10 mm area in a manner that resembled tiles of irradiation spot with 50 micron steps in X and Y directions i. The area proportion of the region with a periodic structure was 50% of the total area.

The following describes how a spatial intensity distribution is shaped by imaging a laser beam. A laser beam is condensed on a space restricting mask configured from a slit or a pinhole via an optical element configured from a lens system or a diffraction optical element for shaping of a spatial intensity distribution. After being shaped into, for example, a triangular, rectangular, pentagonal, hexagonal, or elliptical beam with the space restricting mask, the laser beam is applied to a zirconia ceramic irradiation sample with an imaging optical system at an adjusted magnification. The space distribution may be controlled using a beam shaping optical element that utilizes the diffraction effect and interference, or a beam shaping unit that makes use of, for example, a liquid crystal spatial modulator. In an image transfer method that transfers a spatially controlled shape obtained by using, for example, a slit, not only a flat surface but a three-dimensional surface such as a spherical surface can be processed without a gap with the use of triangular, pentagonal, hexagonal, or other polygonal spatial shapes, other than a rectangle. In this manner, a laser beam is condensed onto a pinhole or a slit of a shape such as a triangle, a rectangle, and a hexagon so that only a region of the laser beam that forms the periodic structure at the irradiated spot can be applied, and a zirconia-based ceramic is continuously irradiated with an optical system adapted to transfer a pinhole image. In this way, it is possible to efficiently lay down spots forming the periodic structure. The beam irradiation site can be changed by varying the relative positions of the applied beam and the irradiated sample. This can be achieved using a method that uses a beam deflector such as a galvano mirror that changes the beam propagation direction, a method that uses a stage that moves the spatial position of the irradiated sample, or a combination of these methods. The method that moves the irradiated sample with a stage enables highly accurate control, whereas the method that uses a beam deflector such as a galvano mirror can find locations faster than the method using a stage. It is desirable to use a beam deflector such as a galvano mirror for processing of a large area.

An Yb-doped laser (1.03 µm, 200 fs) with a Gaussian beam that forms a nearly circular hole with a diameter of 30 microns on target was irradiated by moving the beam in 20-µm steps in vertical and horizontal directions. The laser beam was irradiated 10 shots at each location. This formed a periodic structure over a 1 mm×1 mm area. The area proportion of the periodic structure in the processed area exceeded 50%. A higher area proportion can be achieved by spatially shaping the beam.

The embodiments and examples of implementation discussed above are given for easier understanding of the invention, and the invention is not limited to the embodiments described above.

INDUSTRIAL APPLICABILITY

The present invention is intended to provide a fine periodic structure on a zirconia-based ceramic surface, and is applicable to biomaterials that need to be biocompatible for connection to bone or other body parts. Other examples of areas to which the present invention is applicable include heat-resistant structural materials such as inner walls of a jet engine, and oxygen sensors. This makes the invention highly useful in industry.

REFERENCE SIGNS LIST

1 Laser source
2 Power control unit
3 Polarization control unit
4 Beam shaping unit
5 Condensing lens
6 Irradiation stage

The invention claimed is:

1. A surface structure forming method for zirconia-based ceramics,
   the method comprising irradiating a laser beam to a zirconia-based ceramic surface with a predetermined shot number in one location to form periodic irregularities in a spot of the laser beam irradiation,
   wherein the irradiation of the laser beam with the predetermined shot number in one location forms a periodic structure region with the periodic irregularities and an ablated region where ablation mark is present with no periodic structure, surrounding the periodic structure region in the spot of the laser beam irradiation.

2. The method according to claim 1, wherein the laser beam is condensed to a space restricting mask of a shape that enables irradiating only a beam region that forms the periodic structure, and an image conforming to the shape is transferred to an optical system, and applied to the zirconia-based ceramic surface to lay down a plurality of periodic structure forming regions of said shape.

3. The method according to claim 1,
   wherein the method further comprising repeating the irradiation of the laser beam with the predetermined shot number in one location to form the periodic irregularities in the spot of the laser beam irradiation by moving the laser beam to change the location such that regions of the spots of the laser beam irradiations partially overlap one another, are positioned adjacent to one another, or are positioned away from one another to increase an area of the periodic irregularities.

4. The method according to claim 3,
   wherein the method further comprising restricting a shape of the laser beam with the space restricting mask, and irradiating to a three-dimensional surface, to form a periodic structure over a wide area without a gap of a zirconia base material surface.

5. The method according to claim 4,
wherein the shape of the laser beam is triangular, pentagonal, hexagonal, or other polygonal spatial shapes.

6. The method according to claim 1, wherein a period of the periodic irregularities is not dependent on an incident angle of the laser beam when an s-polarized laser beam is used and the period of the periodic irregularities increases with increase of the incident angle of the laser beam when a p-polarized laser beam is used.

7. The method according to claim 1, wherein the irradiation is operated with a value of an etch rate/a wavelength of the pulsed-laser beam set to be 0.16 to 0.34.

8. A surface structure forming method for a zirconia-based ceramic surface,
the method comprising irradiating a linearly polarized ultrashort pulsed-laser beam to the ceramic surface with a predetermined shot number in one location to form periodic irregularities having a stripe-pattern extending parallel to a direction of polarization of the linearly polarized light in a spot of the laser beam,
wherein the irradiation of the laser beam with the predetermined shot number in one location forms a periodic structure region with the periodic irregularities and an ablated region where ablation mark is present with no periodic structure, surrounding the periodic structure region in the spot of the laser beam irradiation.

9. The method according to claim 8, wherein the laser beam is condensed to a space restricting mask of a shape that enables irradiating only a beam region that forms the periodic structure, and an image conforming to the shape is transferred to an optical system, and applied to the zirconia-based ceramic surface to lay down a plurality of periodic structure forming regions of said shape.

10. The method according to claim 8,
wherein the method further comprising repeating the irradiation of the laser beam with the predetermined shot number in one location to form the periodic irregularities in the spot of the laser beam irradiation by moving the laser beam to change the location such that regions of the spots of the laser beam irradiations partially overlap one another, are positioned adjacent to one another, or are positioned away from one another to increase an area of the periodic irregularities.

11. The method according to claim 10,
wherein the method further comprising restricting a shape of the laser beam with the space restricting mask, and irradiating to a three-dimensional surface, to form a periodic structure over a wide area without a gap of a zirconia base material surface.

12. The method according to claim 11,
wherein the shape of the laser beam is triangular, pentagonal, hexagonal, or other polygonal spatial shapes.

13. The method according to claim 8, wherein a period of the periodic irregularities is not dependent on an incident angle of the laser beam when an s-polarized laser beam is used and the period of the periodic irregularities increases with increase of the incident angle of the laser beam when a p-polarized laser beam is used.

14. The method according to claim 8, wherein the irradiation is operated with a value of an etch rate/a wavelength of the pulsed-laser beam set to be 0.16 to 0.34.

15. A surface structure forming method for a zirconia-based ceramic surface,
the method comprising irradiating a circularly polarized ultrashort pulsed-laser beam to the ceramic surface with a predetermined shot number in one location to form a mesh pattern having periodic raised regions with dot-shaped recessed regions in a spot of the laser beam
wherein the irradiation of the laser beam with the predetermined shot number in one location forms a periodic structure region with the mesh pattern and an ablated region where ablation mark is present with no periodic structure, surrounding the periodic structure region in the spot of the laser beam irradiation.

16. The method according to claim 15, wherein the laser beam is condensed to a space restricting mask of a shape that enables irradiating only a beam region that forms the periodic structure, and an image conforming to the shape is transferred to an optical system, and applied to the zirconia-based ceramic surface to lay down a plurality of periodic structure forming regions of said shape.

17. The method according to claim 15,
wherein the method further comprising repeating the irradiation of the laser beam with the predetermined shot number in one location to form the mesh pattern in the spot of the laser beam irradiation by moving the laser beam to change the location such that regions of the spots of the laser beam irradiations partially overlap one another, are positioned adjacent to one another, or are positioned away from one another to increase an area of the periodic irregularities.

18. The method according to claim 17,
wherein the method comprising restricting a shape of the laser beam with the space restricting mask, and irradiating to a three-dimensional surface, to form a periodic structure over a wide area without a gap of a zirconia base material surface.

19. The method according to claim 18,
wherein the shape of the laser beam is triangular, pentagonal, hexagonal, or other polygonal spatial shapes.

20. The method according to claim 15, wherein the irradiation is operated with a value of an etch rate/a wavelength of the pulsed-laser beam set to be 0.16 to 0.34.

* * * * *